United States Patent
Iloeje et al.

(10) Patent No.: US 12,390,430 B1
(45) Date of Patent: *Aug. 19, 2025

(54) MIRDAMETINIB TREATMENT

(71) Applicant: SpringWorks Therapeutics, Inc., Stamford, CT (US)

(72) Inventors: Uchenna H. Iloeje, Stamford, CT (US); Abraham J. Langseth, Stamford, CT (US); Todd Webster Shearer, Stamford, CT (US)

(73) Assignee: SpringWorks Therapeutics, Inc., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/912,218

(22) Filed: Oct. 10, 2024

Related U.S. Application Data

(60) Provisional application No. 63/663,853, filed on Jun. 25, 2024.

(51) Int. Cl.
*A61K 31/166* (2006.01)
*A61P 25/00* (2006.01)
*A61P 35/00* (2006.01)

(52) U.S. Cl.
CPC ............ *A61K 31/166* (2013.01); *A61P 25/00* (2018.01); *A61P 35/00* (2018.01)

(58) Field of Classification Search
CPC ......... A61K 31/166; A61P 25/00; A61P 35/00
See application file for complete search history.

(56) References Cited

U.S. PATENT DOCUMENTS

| 11,806,321 | B2 | 11/2023 | Iloeje et al. |
| 11,806,322 | B2 | 11/2023 | Iloeje et al. |
| 11,819,487 | B2 | 11/2023 | Iloeje et al. |

OTHER PUBLICATIONS

Armstrong, Amy E., et al. "Treatment decisions and the use of MEK inhibitors for children with neurofibromatosis type 1-related plexiform neurofibromas." BMC cancer 23.1 (2023): 553. (Year: 2023).*

Weiss, Brian D, et al., "NF106: A Neurofibromatosis Clinical Trials Consortium Phase II Trial of the MEK Inhibitor Mirdametinib (PD-0325901) in Adolescents and Adults with NF1-Related Plexiform Neurofibromas", Journal of Clinical Oncology, 2021, 39(7):797-807.

Gross, A A, et al., "Selumetinib in Children with Inoperable Plexiform Neurofibromas", The New England Journal of Medicine, 2020, 1430-1442 and Supplemental Appendix (391 pages).

Sacco, Joseph J, et al., "The Average Body Surface Area of Adult Cancer Patients in the UK: A Multicentre Retrospective Study", PLos One, 2010, 5:1-6, 6 pages.

Armstrong, Amy E, et al., "Treatment decisions and the use of MEK inhibitors for children with neurofibromatosis type 1-related plexiform neurofibromas", BMC Cancer, 2023, 23:553, 13 pages.

* cited by examiner

*Primary Examiner* — Joseph K Mckane
*Assistant Examiner* — Quincy Mckoy
(74) *Attorney, Agent, or Firm* — Blank Rome LLP

(57) ABSTRACT

The present disclosure relates to methods for treating certain types of tumors or cancers, such as plexiform neurofibromas (PN), plexiform neurofibromas associated with neurofibromatosis type 1 (NF1-PN), by administering to a patient in need thereof mirdametinib or a pharmaceutically acceptable salt thereof, such as by a certain dosing scheme.

18 Claims, No Drawings

MIRDAMETINIB TREATMENT

CROSS REFERENCE TO RELATED APPLICATION

This application claims the benefit of U.S. Provisional Application No. 63/663,853 filed Jun. 25, 2024, the entire contents of which are incorporated herein by reference.

FIELD OF THE INVENTION

The present disclosure relates to methods for treating certain types of tumors or cancers, such as plexiform neurofibromas (PN), plexiform neurofibromas associated with neurofibromatosis type 1 (NF1-PN), by administering to a patient in need thereof mirdametinib or a pharmaceutically acceptable salt thereof by a certain dosing scheme.

BACKGROUND

Mirdametinib is an allosteric, small molecule targeting mitogen-activated protein kinase kinase (MEK).

Weiss describes a Phase II clinical trial of mirdametinib in subjects with neurofibromatosis type 1 who have a plexiform neurofibroma (Weiss et al., J. Clin. Oncol., 29, 797-806, 2021).

There is a continuing need for improved treatments for tumors and cancers, including NF1-PN.

BRIEF SUMMARY OF THE INVENTION

One aspect of the present invention is a method of administering mirdametinib to a human patient in need thereof by orally administering to the patient mirdametinib or a pharmaceutically acceptable salt thereof, wherein
  (i) for a patient having a body surface area of 0.4 to 0.69 m$^2$, the patient is initially administered 1 mg mirdametinib twice daily,
  (ii) for a patient having a body surface area of 0.7 to 1.04 m$^2$, the patient is initially administered 2 mg mirdametinib twice daily,
  (iii) for a patient having a body surface area of 1.05 to 1.49 m$^2$, the patient is initially administered 3 mg mirdametinib twice daily, and
  (iv) for a patient having a body surface area of at least 1.5 m$^2$, the patient is initially administered 4 mg mirdametinib twice daily, and wherein the method further comprises one or more of the following:
    (a) upon the patient exhibiting an asymptomatic, absolute decrease in left ventricle ejection fraction (LVEF) of 10% or greater from baseline and is below the lower limit of normal (LLN), withholding the mirdametinib or pharmaceutically acceptable salt thereof until improvement (or, for example, the absolute decrease in LVEF is resolved) and then restarting administration of the mirdametinib or pharmaceutically acceptable salt thereof at a reduced dose;
    (b) upon the patient exhibiting a decrease of 20% or greater in LVEF, permanently discontinuing administration of mirdametinib;
    (c) upon the patient exhibiting a symptomatic retinal pigment epithelium detachment (RPED), withholding the mirdametinib or pharmaceutically acceptable salt thereof until resolution and then restarting administration of the mirdametinib or pharmaceutically acceptable salt thereof at a reduced dose;
    (d) upon the patient exhibiting retinal vein occlusion, permanently discontinuing administration of mirdametinib;
    (e) upon the patient exhibiting a grade 3 or higher dermatitis acneiform or rash, withholding the mirdametinib or pharmaceutically acceptable salt thereof until improvement (or, for example, the dermatitis acneiform is resolved to no higher than a grade 1 dermatitis acneiform or baseline) and then restarting administration of the mirdametinib or pharmaceutically acceptable salt thereof at a reduced dose;
    (f) upon the patient exhibiting any other intolerable grade 2 adverse reaction or grade 3 adverse reaction, withholding the mirdametinib or pharmaceutically acceptable salt thereof until improvement (or, for example, the adverse reaction is resolved to no higher than grade 1 or baseline) and then restarting administration of mirdametinib or pharmaceutically acceptable salt thereof at a reduced dose; and
    (g) upon the patient exhibiting any other grade 4 adverse reaction, withholding the mirdametinib or pharmaceutically acceptable salt thereof until improvement (or, for example, the adverse reaction is resolved to no higher than grade 1 or baseline) and then (x) restarting administration of mirdametinib or pharmaceutically acceptable salt thereof at a reduced dose and (y) optionally considering discontinuing administration of mirdametinib, wherein the reduced dose is:
    (i) for a patient having a body surface area from 0.4 to 0.69 m$^2$, 1 mg once daily (i.e., the dose is reduced from 1 mg twice daily to 1 mg once daily),
    (ii) for a patient having a body surface area from 0.7 to 1.04 m$^2$, 2 mg in the morning, and 1 mg in the evening,
    (iii) for a patient having a body surface area from 1.05 to 1.49 m$^2$, 2 mg in the morning and 2 mg in the evening, and
    (iv) for a patient having a body surface area greater than or equal to 1.5 m$^2$, 3 mg in the morning and 3 mg in the evening. The initial dosage regimen is continued to be used, unless for instance, an adverse event occurs triggering reduction in the dosage regimen.

In one embodiment, the method includes all of (a) through (g).

In one embodiment of any method of any embodiment described herein, the patient suffers from a tumor or cancer. In one embodiment, the tumor or cancer is selected from plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain.

In one embodiment of any of the methods described herein, the patient has plexiform neurofibromas associated with neurofibromatosis type 1 (NF1-PN). In one embodiment, the NF1-PN patient has progressive PN. In one embodiment of any of the methods described herein, the NF1-PN patient has PNs that cause significant morbidity.

In one embodiment of any of the methods described herein, the patient has symptomatic plexiform neurofibromas. In another embodiment of any of the methods described herein, the patient has symptomatic, inoperable plexiform neurofibromas.

In one embodiment of any of the methods described herein, the patient has neurofibromatosis type 1 (NF1)

associated plexiform neurofibromas (PN) that is progressing or causing significant morbidity. In one embodiment of any of the methods described herein, the human patient has neurofibromatosis type 1 (NF1) associated inoperable plexiform neurofibromas (PN) that is progressing or causing significant morbidity. In one embodiment, the patient is a pediatric patient. In another embodiment, the patient is an adult.

In one embodiment of any of the methods described herein, the administration of mirdametinib results in decreased pain intensity.

In one embodiment of any of the methods described herein, the administration of mirdametinib results in decreased pain interference.

Another embodiment is a method of treating an adult or pediatric human patient at least 2 years of age having neurofibromatosis type 1 (NF1) who has symptomatic plexiform neurofibromas (PN) and is in need thereof by orally administering to the patient mirdametinib or a pharmaceutically acceptable salt thereof, wherein
  (i) for a patient having a body surface area of 0.4 to 0.69 m$^2$, the patient is initially administered 1 mg mirdametinib twice daily,
  (ii) for a patient having a body surface area of 0.7 to 1.04 m$^2$, the patient is initially administered 2 mg mirdametinib twice daily,
  (iii) for a patient having a body surface area of 1.05 to 1.49 m$^2$, the patient is initially administered 3 mg mirdametinib twice daily, and
  (iv) for a patient having a body surface area of at least 1.5 m$^2$, the patient is initially administered 4 mg mirdametinib twice daily, and wherein the method further comprises one or more of the following:
  (a) upon the patient exhibiting an asymptomatic, absolute decrease in left ventricle ejection fraction (LVEF) 10% or greater from baseline and is below the lower limit of normal (LLN), withholding the mirdametinib or pharmaceutically acceptable salt thereof until improvement (or, for example, the absolute decrease in LVEF is resolved) and then restarting administration of the mirdametinib or pharmaceutically acceptable salt thereof at a reduced dose;
  (b) upon the patient exhibiting a decrease of 20% or greater in LVEF, permanently discontinuing administration of mirdametinib;
  (c) upon the patient exhibiting a symptomatic retinal pigment epithelium detachment (RPED), withholding the mirdametinib or pharmaceutically acceptable salt thereof until resolution and then restarting administration of the mirdametinib or pharmaceutically acceptable salt thereof at a reduced dose;
  (d) upon the patient exhibiting retinal vein occlusion, permanently discontinuing administration of mirdametinib;
  upon the patient exhibiting a grade 3 or higher dermatitis acneiform or rash, withholding the mirdametinib or pharmaceutically acceptable salt thereof until improvement (or, for example, the dermatitis acneiform is resolved to no higher than a grade 1 dermatitis acneiform or baseline) and then restarting administration of the mirdametinib or pharmaceutically acceptable salt thereof at a reduced dose;
  (f) upon the patient exhibiting any other intolerable grade 2 or grade 3 adverse reaction, withholding the mirdametinib or pharmaceutically acceptable salt thereof until improvement (or, for example, the adverse reaction is resolved to no higher than grade 1 or baseline) and then restarting administration of mirdametinib or pharmaceutically acceptable salt thereof at a reduced dose; and
  (g) upon the patient exhibiting any other grade 4 adverse reaction, withholding the mirdametinib or pharmaceutically acceptable salt thereof until improvement (or, for example, the adverse reaction is resolved to no higher than grade 1 or baseline) and then (x) restarting administration of mirdametinib or pharmaceutically acceptable salt thereof at a reduced dose and (y) optionally considering discontinuing administration of mirdametinib, wherein the reduced dose is:
  (i) for a patient having a body surface area from 0.4 to 0.69 m$^2$, 1 mg once daily,
  (ii) for a patient having a body surface area from 0.7 to 1.04 m$^2$, 2 mg in the morning, and 1 mg in the evening,
  (iii) for a patient having a body surface area from 1.05 to 1.49 m$^2$, 2 mg in the morning and 2 mg in the evening, and
  (iv) for a patient having a body surface area greater than or equal to 1.5 m$^2$, 3 mg in the morning and 3 mg in the evening.

In one embodiment of any method of any embodiment described herein, (a) upon the patient exhibiting an asymptomatic, absolute decrease in left ventricle ejection fraction (LVEF) of 10% or greater and no more than 20% from baseline and is below the lower limit of normal (LLN), withholding the mirdametinib or pharmaceutically acceptable salt thereof until the absolute decrease in LVEF is resolved and then restarting administration of the mirdametinib or pharmaceutically acceptable salt thereof at the reduced dose.

In one embodiment of any method of any embodiment described herein, the adverse reaction in (f) or (g) is selected from diarrhea, abdominal pain, and fatigue.

In one embodiment of any method of any embodiment described herein, (g) upon the patient exhibiting any grade 4 adverse reaction, permanently discontinuing administration of mirdametinib.

In one embodiment of any method of any embodiment described herein, the patient is an adult.

In one embodiment of any method of any embodiment described herein, the patient is a pediatric patient.

Another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein (i) the patient exhibits, at steady state exposure from administration of mirdametinib or a pharmaceutically acceptable salt thereof, a $C_{max}$ of mirdametinib of from about 95 to about 280 ng/ml or from about 100 to about 500 ng/ml (such as from about 130 to about 245, from about 150 to about 230, or from about 160 to about 215 ng/mL), prior to withholding the mirdametinib or pharmaceutically acceptable salt thereof, and (ii) after the patient has an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient 1 mg of mirdametinib or a pharmaceutically acceptable salt thereof daily (e.g., 1 mg once daily).

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein (i) the patient exhibits, at steady state exposure from administration of mirdametinib or a pharmaceutically acceptable salt thereof, a $C_{max}$ of mirdametinib of from about 95 to about 280 ng/ml or from about 100 to about 500 ng/ml (such as from about 130 to about 245, from about 150 to about 230, or from about 160 to about 215 ng/mL), prior to withholding the mirdametinib or pharmaceutically acceptable salt thereof, and (ii) after the patient has a grade 3 or higher dermatitis acneiform or rash, withholding the mirdametinib or pharmaceutically acceptable salt thereof until improvement to no higher than a grade 1.

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein (i) the patient exhibits, at steady state exposure from administration of mirdametinib or a pharmaceutically acceptable salt thereof, a $AUC_{last}$ of mirdametinib of from about 200 to about 720 ng h/mL (such as from about 250 to about 610, from about 250 to about 670, from about 350 to about 510, from about 350 to about 660, from about 380 to about 700, from about 380 to about 480, or from about 410 to about 510 ng h/mL), prior to withholding the mirdametinib or pharmaceutically acceptable salt thereof, and (ii) after the patient has an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient 1 mg of mirdametinib or a pharmaceutically acceptable salt thereof daily (e.g., 1 mg once daily).

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein (i) the patient exhibits, at steady state exposure from administration of mirdametinib or a pharmaceutically acceptable salt thereof, a $AUC_{last}$ of mirdametinib of from about 200 to about 720 ng h/mL (such as from about 250 to about 610, from about 250 to about 670, from about 350 to about 510, from about 350 to about 660, from about 380 to about 700, from about 380 to about 480, or from about 410 to about 510 ng·h/mL), prior to withholding the mirdametinib or pharmaceutically acceptable salt thereof, and (ii) after the patient has a grade 3 or higher dermatitis acneiform or rash, withholding the mirdametinib or pharmaceutically acceptable salt thereof until improvement to no higher than a grade 1 and then administering to the patient 1 mg of mirdametinib or a pharmaceutically acceptable salt thereof daily (e.g., 1 mg once daily).

Yet another embodiment is a method of treating an adult or pediatric patient at least 2 years of age having neurofibromatosis type 1 (NF1) who has symptomatic plexiform neurofibromas (PN) and is in need thereof. The method comprises orally administering to the patient mirdametinib or a pharmaceutically acceptable salt thereof, wherein after the patient has an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient 1 mg of mirdametinib or a pharmaceutically acceptable salt thereof daily (e.g., 1 mg once daily), wherein the patient has a body surface area from 0.4 to 0.69 m².

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein after the patient has a grade 3 or higher dermatitis acneiform or rash, withholding the mirdametinib or pharmaceutically acceptable salt thereof until improvement to no higher than a grade 1 and then administering to the patient 1 mg of mirdametinib or a pharmaceutically acceptable salt thereof once daily, wherein the patient has a body surface area from 0.4 to 0.69 m².

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein after the patient has an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient 3 mg of mirdametinib or a pharmaceutically acceptable salt thereof daily, wherein the patient has a body surface area from 0.7 to 1.04 m² (such as 2 mg in the morning, and 1 mg in the evening).

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein after the patient has a grade 3 or higher dermatitis acneiform or rash, withholding the mirdametinib or pharmaceutically acceptable salt thereof until improvement to no higher than a grade 1 and then administering to the patient 3 mg of mirdametinib or a pharmaceutically acceptable salt thereof daily (such as 2 mg in the morning, and 1 mg in the evening), wherein the patient has a body surface area from 0.7 to 1.04 m².

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein after the patient has an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient 4 mg of mirdametinib or a pharmaceutically acceptable salt thereof daily (such as 2 mg in the morning, and 2 mg in the evening), wherein the patient has a body surface area from 1.05 to 1.49 m².

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein after the patient has a grade 3 or higher dermatitis acneiform or rash, withholding the mirdametinib or pharmaceutically acceptable salt thereof until improvement to no higher than a grade 1 and then administering to the patient 4 mg of mirdametinib or a pharmaceutically acceptable salt thereof daily (such as 2 mg in the morning, and 2 mg in the evening), wherein the patient has a body surface area from 1.05 to 1.49 m².

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein after the patient has an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient 6 mg of mirdametinib or a pharmaceutically acceptable salt thereof daily (such as 3 mg in the morning, and 3 mg in the evening), wherein the patient has a body surface area greater than or equal to 1.5 m².

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein after the patient has a grade 3 or higher dermatitis acneiform or rash, withholding the mirdametinib or pharmaceutically acceptable salt thereof until improvement to no higher than a grade 1 and then administering to the patient 6 mg of mirdametinib or a pharmaceutically acceptable salt thereof daily (such as 3 mg in the morning, and 3 mg in the evening), wherein the patient has a body surface area greater than or equal to 1.5 m².

Yet another embodiment is a method of treating an adult or pediatric patient at least 2 years of age having neurofibromatosis type 1 (NF1) who has symptomatic plexiform neurofibromas (PN) and is in need thereof. The method comprises orally administering to the patient an effective amount of mirdametinib or a pharmaceutically acceptable salt thereof, wherein (i) the patient exhibits, at steady state exposure from administration of mirdametinib or a pharmaceutically acceptable salt thereof, a $C_{max}$ of mirdametinib of from about 95 to about 280 ng/ml or from about 100 to about 500 ng/mL, and (ii) upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering
  (i) for a patient having a body surface area from 0.4 to 0.69 m², 1 mg once daily,
  (ii) for a patient having a body surface area from 0.7 to 1.04 m², 2 mg in the morning, and 1 mg in the evening,
  (iii) for a patient having a body surface area from 1.05 to 1.49 m², 2 mg in the morning and 2 mg in the evening, and
  (iv) for a patient having a body surface area greater than or equal to 1.5 m², 3 mg in the morning and 3 mg in the evening. In one embodiment, the patient exhibits an asymptomatic, absolute decrease in LVEF of 10% or greater and no more than 20% from baseline and is below the LLN.

Yet another embodiment is a method of treating an adult or pediatric patient at least 2 years of age having neurofibromatosis type 1 (NF1) who has symptomatic plexiform neurofibromas (PN) and is in need thereof. The method comprises orally administering to the patient an effective amount of mirdametinib or a pharmaceutically acceptable salt thereof, wherein
  (a) the patient exhibits, at steady state exposure from administration of mirdametinib or a pharmaceutically acceptable salt thereof, a $C_{max}$ of mirdametinib of from about 95 to about 280 ng/mL or 100 to about 500 ng/ml, and
  (b) upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then restarting administration of the mirdametinib or pharmaceutically acceptable salt thereof at a reduced dose;
  (c) upon the patient exhibiting a decrease of 20% or greater in LVEF, permanently discontinuing administration of mirdametinib;
  (d) upon the patient exhibiting a symptomatic retinal pigment epithelium detachment (RPED), withholding the mirdametinib or pharmaceutically acceptable salt thereof until resolution and then restarting administration of the mirdametinib or pharmaceutically acceptable salt thereof at a reduced dose;
  (e) upon the patient exhibiting retinal vein occlusion, permanently discontinuing administration of mirdametinib;
  (f) upon the patient exhibiting a grade 3 or higher dermatitis acneiform or rash, withholding the mirdametinib or pharmaceutically acceptable salt thereof until improvement and then restarting administration of the mirdametinib or pharmaceutically acceptable salt thereof at a reduced dose;
  (g) upon the patient exhibiting any other intolerable grade 2 or grade 3 adverse reaction, withholding the mirdametinib or pharmaceutically acceptable salt thereof until improvement and then restarting administration of mirdametinib or pharmaceutically acceptable salt thereof at a reduced dose; and
  (h) upon the patient exhibiting any other grade 4 adverse reaction, withholding the mirdametinib or pharmaceutically acceptable salt thereof until improvement and then (x) restarting administration of mirdametinib or pharmaceutically acceptable salt thereof at a reduced dose, wherein the reduced dose is:
    (i) for a patient having a body surface area from 0.4 to 0.69 m², 1 mg once daily,
    (ii) for a patient having a body surface area from 0.7 to 1.04 m², 2 mg in the morning, and 1 mg in the evening,
    iii) for a patient having a body surface area from 1.05 to 1.49 m², 2 mg in the morning and 2 mg in the evening, and
    (iv) for a patient having a body surface area greater than or equal to 1.5 m², 3 mg in the morning and 3 mg in the evening.

Yet another embodiment is a method of treating an adult or pediatric patient at least 2 years of age having neurofibromatosis type 1 (NF1) who has symptomatic plexiform neurofibromas (PN) and is in need thereof. The method comprises orally administering to the patient mirdametinib or a pharmaceutically acceptable salt thereof, wherein (i) the patient exhibits, at steady state exposure from administration of mirdametinib or a pharmaceutically acceptable salt thereof, an $AUC_{last}$ of mirdametinib of from about 200 to about 720 ng h/mL, and (ii) upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering (i) for a patient having a body surface area from 0.4 to 0.69 m$^2$, 1 mg once daily,
(ii) for a patient having a body surface area from 0.7 to 1.04 m$^2$, 2 mg in the morning, and 1 mg in the evening,
(iii) for a patient having a body surface area from 1.05 to 1.49 m$^2$, 2 mg in the morning and 2 mg in the evening, and
(iv) for a patient having a body surface area greater than or equal to 1.5 m$^2$, 3 mg in the morning and 3 mg in the evening. Yet another embodiment is a method of treating a patient at least 2 years of age having neurofibromatosis type 1 (NF1) who has symptomatic plexiform neurofibromas (PN) and is in need thereof. The method comprises orally administering to the patient a daily dose of 2 mg of mirdametinib or a pharmaceutically acceptable salt thereof, wherein upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient a reduced daily dose of 1 mg of mirdametinib or the pharmaceutically acceptable salt thereof. The 2 mg daily dose can be administered to the patient as, for example, two 1 mg dosages of mirdametinib or a pharmaceutically acceptable salt thereof (e.g., 1 mg in the morning and 1 mg in the evening). The 1 mg reduced daily dose can administered to the patient, for example, once daily.

Yet another embodiment is a method of treating a patient at least 2 years of age having neurofibromatosis type 1 (NF1) who has symptomatic plexiform neurofibromas (PN) and is in need thereof, the method comprising orally administering to the patient a daily dose of 4 mg of mirdametinib or a pharmaceutically acceptable salt thereof, wherein upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient a reduced daily dose of 3 mg of mirdametinib or the pharmaceutically acceptable salt thereof. The 4 mg daily dose can be administered to the patient as, for example, two 2 mg dosages of mirdametinib or a pharmaceutically acceptable salt thereof (e.g., 2 mg in the morning and 2 mg in the evening). The 3 mg reduced daily dose can administered to the patient, for example, as a 2 mg dosage in the morning and a 1 mg dosage in the evening.

Yet another embodiment is a method of treating a patient at least 2 years of age having neurofibromatosis type 1 (NF1) who has symptomatic plexiform neurofibromas (PN) and is in need thereof, the method comprising orally administering to the patient a daily dose of 6 mg of mirdametinib or a pharmaceutically acceptable salt thereof, wherein upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient a reduced daily dose of 4 mg of mirdametinib or the pharmaceutically acceptable salt thereof. The 6 mg daily dose can be administered to the patient as, for example, two 3 mg dosages of mirdametinib or a pharmaceutically acceptable salt thereof (e.g., 13 mg in the morning and 3 mg in the evening). The 4 mg reduced daily dose can administered to the patient, for example, as a 2 mg dosage in the morning and a 2 mg dosage in the evening.

Yet another embodiment is a method of treating a patient at least 2 years of age having neurofibromatosis type 1 (NF1) who has symptomatic plexiform neurofibromas (PN) and is in need thereof, the method comprising orally administering to the patient a daily dose of 8 mg of mirdametinib or a pharmaceutically acceptable salt thereof, wherein upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient a reduced daily dose of 6 mg of mirdametinib or the pharmaceutically acceptable salt thereof. The 8 mg daily dose can be administered to the patient as, for example, two 4 mg dosages of mirdametinib or a pharmaceutically acceptable salt thereof (e.g., 4 mg in the morning and 4 mg in the evening). The 6 mg reduced daily dose can administered to the patient, for example, as a 3 mg dosage in the morning and a 3 mg dosage in the evening.

Yet another embodiment is a method of treating a patient at least 2 years of age having a tumor or cancer and in need thereof, the method comprising orally administering to the patient mirdametinib or a pharmaceutically acceptable salt thereof, wherein upon the patient exhibiting a symptomatic retinal pigment epithelium detachment (RPED), withholding the mirdametinib or pharmaceutically acceptable salt thereof until resolution and then administering the mirdametinib or pharmaceutically acceptable salt thereof at a reduced dose, wherein the reduced dose is:

(i) for a patient having a body surface area from 0.4 to 0.69 m$^2$, 1 mg of mirdametinib or a pharmaceutically acceptable salt thereof once daily,
(ii) for a patient having a body surface area from 0.7 to 1.04 m$^2$, 2 mg of mirdametinib or a pharmaceutically acceptable salt thereof in the morning, and 1 mg of mirdametinib or a pharmaceutically acceptable salt thereof in the evening,
(iii) for a patient having a body surface area from 1.05 to 1.49 m$^2$, 2 mg of mirdametinib or a pharmaceutically acceptable salt thereof in the morning and 2 mg of mirdametinib or a pharmaceutically acceptable salt thereof in the evening, and
(iv) for a patient having a body surface area greater than or equal to 1.5 m$^2$, 3 mg of mirdametinib or a pharmaceutically acceptable salt thereof in the morning and 3 mg of mirdametinib or a pharmaceutically acceptable salt thereof in the evening. In some instances, upon the patient exhibiting retinal vein occlusion, the method comprises permanently discontinuing administration of mirdametinib. In some instances, is the patient exhibits an asymptomatic, absolute decrease in left ventricle ejection fraction (LVEF) of 10% or greater from baseline and is below the lower limit of normal (LLN), the method may further comprise withholding the mirdametinib or pharmaceutically acceptable salt thereof until improvement and then restarting administration of the mirdametinib or pharmaceutically acceptable salt thereof at the reduced dose. In some instances, the patient exhibits an asymptomatic, absolute decrease in LVEF of 10% or greater and no more than 20% from baseline and is below the LLN. In some instances, the patient exhibits, at steady state exposure from administration of mirdametinib or a pharmaceutically acceptable salt thereof, a $AUC_{last}$ of mirdametinib of from about 200 to about 720 ng h/mL, prior to the patient exhibiting a symptomatic RPED. In some instances, the patient exhibits, at steady state exposure from administration of mirdametinib or a pharmaceutically acceptable salt thereof, a $C_{max}$ of mirdametinib of from about 95 to about 280 ng/mL, prior to the patient exhibiting a symptomatic RPED.

Yet another embodiment is a method of treating a patient at least 2 years of age having neurofibromatosis type 1 (NF1) who has symptomatic plexiform neurofibromas (PN), the method comprising orally administering to the patient mirdametinib or a pharmaceutically acceptable salt thereof, wherein
(i) for a patient having a body surface area of 0.4 to 0.69 $m^2$, the patient is initially administered 1 mg mirdametinib or a pharmaceutically acceptable salt thereof twice daily,
(ii) for a patient having a body surface area of 0.7 to 1.04 $m^2$, the patient is initially administered 2 mg mirdametinib or a pharmaceutically acceptable salt thereof twice daily,
(iii) for a patient having a body surface area of 1.05 to 1.49 $m^2$, the patient is initially administered 3 mg mirdametinib or a pharmaceutically acceptable salt thereof twice daily, and
(iv) for a patient having a body surface area of at least 1.5 $m^2$, the patient is initially administered 4 mg mirdametinib or a pharmaceutically acceptable salt thereof twice daily, and wherein upon the patient exhibiting a symptomatic retinal pigment epithelium detachment (RPED), withholding the mirdametinib or pharmaceutically acceptable salt thereof until resolution and then administering the mirdametinib or pharmaceutically acceptable salt thereof at a reduced dose, wherein the reduced dose is:
(I) for a patient having a body surface area from 0.4 to 0.69 $m^2$, 1 mg of mirdametinib or a pharmaceutically acceptable salt thereof once daily,
(II) for a patient having a body surface area from 0.7 to 1.04 $m^2$, 2 mg of mirdametinib or a pharmaceutically acceptable salt thereof in the morning, and 1 mg of mirdametinib or a pharmaceutically acceptable salt thereof in the evening,
(III) for a patient having a body surface area from 1.05 to 1.49 $m^2$, 2 mg of mirdametinib or a pharmaceutically acceptable salt thereof in the morning and 2 mg of mirdametinib or a pharmaceutically acceptable salt thereof in the evening, and
(IV) for a patient having a body surface area greater than or equal to 1.5 $m^2$, 3 mg of mirdametinib or a pharmaceutically acceptable salt thereof in the morning and 3 mg of mirdametinib or a pharmaceutically acceptable salt thereof in the evening. In some instances, upon the patient exhibiting retinal vein occlusion, the method comprises permanently discontinuing administration of mirdametinib. In some instances, is the patient exhibits an asymptomatic, absolute decrease in left ventricle ejection fraction (LVEF) of 10% or greater from baseline and is below the lower limit of normal (LLN), the method may further comprise withholding the mirdametinib or pharmaceutically acceptable salt thereof until improvement and then restarting administration of the mirdametinib or pharmaceutically acceptable salt thereof at the reduced dose. In some instances, the patient exhibits an asymptomatic, absolute decrease in LVEF of 10% or greater and no more than 20% from baseline and is below the LLN. In some instances, the patient exhibits, at steady state exposure from administration of mirdametinib or a pharmaceutically acceptable salt thereof, a $AUC_{last}$ of mirdametinib of from about 200 to about 720 ng h/mL, prior to the patient exhibiting a symptomatic RPED. In some instances, the patient exhibits, at steady state exposure from administration of mirdametinib or a pharmaceutically acceptable salt thereof, a $C_{max}$ of mirdametinib of from about 95 to about 280 ng/mL, prior to the patient exhibiting a symptomatic RPED.

In one embodiment of any method of any embodiment described herein, the patient exhibits, at steady state exposure from administration of mirdametinib or a pharmaceutically acceptable salt thereof, a $C_{max}$ of mirdametinib of from about 95 to about 280 ng/ml or from about 100 to about 500 ng/ml (such as from about 130 to about 245, from about 150 to about 230, or from about 160 to about 215 ng/ml), prior to withholding the mirdametinib or pharmaceutically acceptable salt thereof.

In one embodiment of any method of any embodiment described herein, the patient exhibits, at steady state exposure from administration of mirdametinib or a pharmaceutically acceptable salt thereof, a $AUC_{last}$ of mirdametinib of from about 200 to about 720 ng h/mL (such as from about 250 to about 610, from about 250 to about 670, from about 350 to about 510, from about 350 to about 660, from about 380 to about 700, from about 380 to about 480, or from about 410 to about 510 ng h/mL), prior to withholding the mirdametinib or pharmaceutically acceptable salt thereof.

In one embodiment of any method of any embodiment described herein, the the mirdametinib or pharmaceutically acceptable salt thereof is administered in free base form (i.e., as mirdametinib).

In one embodiment of any method of any embodiment described herein, the mirdametinib or pharmaceutically acceptable salt thereof is administered with or without food.

In one embodiment of any method of any embodiment described herein, if a patient misses a dose of mirdametinib, the patient skips that dose and resumes administration at the next scheduled dose.

In one embodiment of any method of any embodiment described herein, if vomiting occurs after administering a dose of mirdametinib, the patient does not administer an additional dose of mirdametinib, but continues with administration at the next scheduled dose.

In some embodiments directed towards any of the methods described herein, wherein the patient is an adult patient having neurofibromatosis type 1 (NF1) who has symptomatic plexiform neurofibromas (PN).

In some embodiments directed towards any of the methods described herein, wherein the patient is a pediatric patient having neurofibromatosis type 1 (NF1) who has symptomatic plexiform neurofibromas (PN).

In some embodiments directed towards any of the methods described herein, wherein the mirdametinib or pharmaceutically acceptable salt thereof is administered for the first 21 days or each 28-day cycle.

In some embodiments directed towards any of the methods described herein, wherein the mirdametinib or pharmaceutically acceptable salt thereof is administered until plexiform neurofibromas progression or unacceptable toxicity.

In one embodiment of any of the methods described herein, the treatment results in decreased pain intensity.

In one embodiment of any of the methods described herein, the treatment results in decreased pain interference.

In one embodiment of any method of any embodiment described herein, the patient is an adult patient having neurofibromatosis type 1 (NF1) who has symptomatic plexiform neurofibromas (PN).

In one embodiment of any method of any embodiment described herein, the patient is a pediatric patient having neurofibromatosis type 1 (NF1) who has symptomatic plexiform neurofibromas (PN).

In one embodiment of any method of any embodiment described herein, the mirdametinib or pharmaceutically acceptable salt thereof is administered for the first 21 days of each 28-day cycle.

In one embodiment of any method of any embodiment described herein, the mirdametinib or pharmaceutically acceptable salt thereof is administered until plexiform neurofibromas progression or unacceptable toxicity.

In one embodiment of any method of any embodiment described herein, the left ventricle ejection fraction (LVEF) is assessed by echocardiogram prior to initiating treatment with mirdametinib and every 3 months during the first year of treatment with mirdametinib.

In one embodiment of any method of any embodiment described herein, a comprehensive ophthalmic assessment is conducted prior to initiating treatment with mirdametinib and at regular intervals during treatment with mirdametinib, and for new or worsening visual changes.

In one embodiment of any method of any embodiment described herein, the patient has symptomatic plexiform neurofibromas (e.g., symptomatic, inoperable plexiform neurofibromas).

In one embodiment of any method of any embodiment described herein, the patient has progressive plexiform neurofibromas.

In one embodiment of any method of any embodiment described herein, the patient has plexiform neurofibromas that cause significant morbidity.

In one embodiment of any method of any embodiment described herein, the NF1-PN patient has head and neck lesions that are compromising the airway or great vessels, brachial or lumbar plexus lesions that are causing nerve compression and loss of function, lesions causing major deformity or are significantly disfiguring, lesions of the extremity that cause limb hypertrophy or loss of function or painful lesions. In one embodiment, the lesions causing major deformity or are significantly disfiguring are tumors of the head and neck or those on other areas of the body that are unable to be concealed by standard garments. In one embodiment of any method of any embodiment described herein, the patient has paraspinal lesions.

In one embodiment of any of the methods described herein, the patient has the clinical diagnosis of NF1 using the NIH Consensus Conference and one or more of the following:
 (a) six or more café-au-lait macules with a diameter >5 mm in prepubertal and >15 mm in post-pubertal individuals;
 (b) freckling in axilla or inguinal regions;
 (c) optic glioma;
 (d) two or more Lisch nodules;
 (e) a distinctive bony lesion (dysplasia of the sphenoid bone or dysplasia of thinning of long bone cortex); and
 (f) a first degree relative with NF1.

In one embodiment of any of the methods described herein, the patient has a constitutional NF1 mutation documented in a Clinical Laboratory Improvement Amendments/College of American Pathologists certified lab.

In one embodiment of any of the methods described herein, the patient either (a) has a parent diagnosed with NF1 and one or more criteria of (1) through (7) or (b) does not have a parent diagnosed with NF1 but has two or more criteria of (1) through (7):
 (1) six or more café-au-lait macules over 5 mm in greatest diameter in prepubertal individuals and over 15 mm in greatest diameter in post-pubertal individuals;
 (2) freckling in the axillary or inguinal region;
 (3) two or more neurofibromas of any type or one plexiform neurofibroma
 (4) optic pathway glioma;
 (5) two or more iris Lisch nodules identified by slit lamp examination or two or more choroidal abnormalities (defined as bright, patchy nodules imaged by optical coherence tomography (OCT)/near-infrared reflectance (NIR) imaging;
 (6) a distinctive osseus lesion (such as sphenoid dysplasia, anterolateral bowing of the tibia, or pseudarthrosis of a long bone); and
 (7) a heterozygous pathogenic NF1 variant with a variant allele fraction of 50% in apparently normal tissue such as white blood cells.

In one embodiment of any of the methods described herein, over each four week period, the mirdametinib is administered for the first three weeks and discontinued for the last one week.

In one embodiment, the adverse event resulting in the dose reduction is acneiform. In another embodiment, the adverse event resulting in the dose reduction is dermatitis acneiform. In yet another embodiment, the adverse event resulting in the dose reduction is dermatitis acneiform, diarrhea, or nausea. In yet another embodiment, the adverse event resulting in the dose reduction in a pediatric patient is decreased neutrophil count.

In one embodiment of any of the methods described herein, the patient has at least a 20% reduction in plexiform neurofibroma volume as determined by volumetric magnetic resonance imaging analysis following treatment with mirdametinib.

In one embodiment of any of the methods described herein, the patient permanently discontinues treatment with mirdametinib due to a grade 4 adverse reaction where the adverse reaction is abdominal pain, constipation, dermatitis acneiform, or diarrhea. In one embodiment of any of the methods described herein, the pediatric patient permanently discontinues treatment with mirdametinib due to a grade 4 adverse reaction where the adverse reaction is abdominal pain, constipation, dermatitis acneiform, or diarrhea.

In one embodiment of any method of any embodiment described herein, the patient exhibits, at steady state exposure from administration of mirdametinib or a pharmaceutically acceptable salt thereof, a $C_{max}$ of mirdametinib from about 95 or 100 ng/ml to about 500 ng/ml. In one embodiment, the patient exhibits, at steady state exposure from administration of mirdametinib or a pharmaceutically acceptable salt thereof, a $C_{max}$ of mirdametinib of from about 95 to about 280 ng/ml (such as from about 130 to about 245, from about 150 to about 230, or from about 160 to about 215 ng/mL), prior to withholding the mirdametinib or pharmaceutically acceptable salt thereof.

In one embodiment of any method of any embodiment described herein, the patient exhibits, at steady state exposure from administration of mirdametinib or a pharmaceutically acceptable salt thereof, a $AUC_{last}$ of mirdametinib of from about 200 to about 720 ng·h/mL (such as from about 250 to about 610, from about 250 to about 670, from about 350 to about 510, from about 350 to about 660, from about 380 to about 700, from about 380 to about 480, or from about 410 to about 510 ng h/mL), prior to withholding the mirdametinib or pharmaceutically acceptable salt thereof.

In one embodiment of any of the methods described herein, the patient is 2 to 15 years of age.

In one embodiment of any of the methods described herein, the method further comprises prior to treatment (i) determining whether to select mirdametinib as a treatment for the patient, and (ii) selecting mirdametinib as a treatment for the patient at least partially based on its objective response rate, where the objective response rate is defined as at least a 20% decrease in tumor size using centrally read MRI volumetric analysis (for example, per Response Evaluation in Neurofibromatosis and Schwannomatosis (REINS) criteria). In one embodiment, in step (i), mirdametinib is selected based on a response rate of at least 40% in adult patients, such as an objective response rate of 41%. In another embodiment, in step (i), mirdametinib is selected based on a response rate of at least 50% in pediatric patients, such as an objective response rate of 52%.

Methods for treating a tumor or cancer selected from the group consisting of plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain, comprising administering to a patient in need thereof mirdametinib or a pharmaceutically acceptable salt thereof are also provided herein. The mirdametinib or a pharmaceutically acceptable salt thereof may be administered according to the dosing scheme described herein.

In some aspects, a therapeutically effective amount of mirdametinib, or a pharmaceutically acceptable salt thereof, is administered. In some aspects, the mirdametinib, or a pharmaceutically acceptable salt thereof, is administered in an amount of about 1 mg/m² to about 10 mg/m² per day, such as about 2 mg/m² per day, based on mirdametinib free base.

In some aspects, the mirdametinib, or a pharmaceutically acceptable salt thereof, is administered once daily. In some aspects, the mirdametinib, or a pharmaceutically acceptable salt thereof, is administered twice daily.

In some aspects, the mirdametinib, or a pharmaceutically acceptable salt thereof, exhibits high blood-brain-barrier penetration.

In some aspects, the patient is a human. In some aspects, the human has an age of ≥2 and <25.

In one embodiment of any of the methods described herein, the human patient has had no prior exposure to MEK inhibitors.

In one embodiment of any of the methods described herein, the mirdametinib, or a pharmaceutically acceptable salt thereof, is administered orally. In some aspects, the mirdametinib, or a pharmaceutically acceptable salt thereof, is dispersible (e.g., a dispersible tablet such as described in U.S. Pat. No. 11,571,402, which is hereby incorporated by reference) in a potable liquid (e.g., about 5 to about 10 mL of water) or orodispersible in a patient's saliva. In some aspects, the mirdametinib, or a pharmaceutically acceptable salt thereof, is administered orally as a solid dosage form. In some aspects, the solid dosage form is a tablet or capsule. In some aspects, the solid dosage form is a capsule.

In one embodiment of any of the methods described herein, the mirdametinib, or a pharmaceutically acceptable salt thereof, is administered as a monotherapy to treat the tumor or cancer. In some aspects, the mirdametinib, or a pharmaceutically acceptable salt thereof, is administered in combination with another active ingredient and/or surgery to treat the tumor or cancer.

In one embodiment of any of the methods described herein, the mirdametinib is mirdametinib free base.

DETAILED DESCRIPTION OF THE INVENTION

I. Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "mirdametinib" refers to the single enantiomer N-((R)-2,3-dihydroxypropoxy)-3,4-difluoro-2-(2-fluoro-4-iodo-phenylamino)-benzamide. The teachings throughout the specification regarding mirdametinib equally apply to pharmaceutically acceptable salts of mirdametinib. For instance, the disclosure of a method of treating neurofibromatosis type 1 (NF1) associated inoperable plexiform neurofibromas (PN) with mirdametinib also means that a pharmaceutically acceptable salt of mirdametinib can be administered to treat NF1 associated inoperable PN.

The term "mg/m²" refers to the dose in milligrams per m² body surface area of the patient.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject. The patient may be a pediatric patient.

The term "pediatric" refers to a human subject under the age of 21 years at the time of treatment. The term "pediatric" can be further divided into various subpopulations including: neonates (from birth through the first 28 days of life);

infants (29 days of age to less than two years of age); children (two years of age to less than 12 years of age); and adolescents (12 years of age through 21 years of age (up to, but not including, the twenty-second birthday)). See, e.g., Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. Younger pediatric patients in particular, such as neonates, infants and young children, can have difficulty swallowing whole capsules or tablets.

The term "dispersible" as used herein refers to a composition (e.g., a tablet, powder, granules, minitablets, or pellets) which disintegrates and/or dissolves when combined with water or another potable liquid (e.g., a non-water beverage), or a subject's own saliva when placed in the subject's mouth, with or without the addition of agitation or temperature modification. In some aspects, the dispersible composition disintegrates or dissolves within 10 minutes, 9 minutes, 8 minutes, 7 minutes, 6 minutes, 5 minutes, 4 minutes, 3 minutes, 2 minutes, or 1 minute after being combined with water or another potable liquid. Such disintegration or dissolution need not be complete. For example, a dispersible tablet may dissolve almost entirely, but some undissolved particulate matter may remain.

The term "orodispersible" refers to a composition which is capable of dissolving or disintegrating in a subject's mouth (i.e., dissolving or disintegrating in a subject's saliva) if administered orally, without a requirement of first dissolving or disintegrating in a separate container.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for a tumor, according to the methods described herein if the patient shows one or more of the following: a reduction in the size of the tumor; relief of one or more symptoms associated with the specific tumor; a reduction in the volume of the tumor; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given tumor can be used to determine whether an effective amount of mirdametinib meets any of these particular endpoints (e.g., CR, PFS, PR).

In certain aspects, a subject is successfully "treated" for cancer, e.g., ovarian cancer, according to the methods described herein if the patient shows one or more of the following: a reduction in the number of or complete absence of cancer cells; relief of one or more symptoms associated with the specific cancer; reduced morbidity and mortality; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given cancer can be used to determine whether an effective amount of mirdametinib meets any of these particular endpoints (e.g., CR, PFS, PR).

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy,* 21st Edition, Lippincott Williams & Wilkins: Philadelphia, PA, 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; Pharmaceutical Preformulation and Formulation, Gibson Ed., CRC Press LLC: Boca Raton, FL, 2004 (incorporated herein by reference).

The term "pharmaceutically-acceptable salts" refers to the relatively non-toxic, inorganic and organic acid addition salts of mirdametinib. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts. See, e.g., Berge et al. (1977) "Pharmaceutical Salts", J. Pharm. Sci. 66:1-19.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, and isothionic.

The term "baseline" refers to an initial measurement of a condition that is taken at an early time point and used for comparison over time to look for changes. Baseline may be a measurement just before treatment and used afterwards to see if the treatment had an effect. For example, the size of a tumor can be measured before treatment (baseline) and then afterwards to see if the treatment had an effect.

The terms "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

II. Methods of Treatment

One aspect of the present invention is a method of administering mirdametinib to a human patient in need thereof by orally administering to the patient mirdametinib or a pharmaceutically acceptable salt thereof, wherein
  (i) for a patient having a body surface area of 0.4 to 0.69 $m^2$, the patient is initially administered 1 mg mirdametinib twice daily,
  (ii) for a patient having a body surface area of 0.7 to 1.04 $m^2$, the patient is initially administered 2 mg mirdametinib twice daily,
  (iii) for a patient having a body surface area of 1.05 to 1.49 $m^2$, the patient is initially administered 3 mg mirdametinib twice daily, and
  (iv) for a patient having a body surface area of at least 1.5 $m^2$, the patient is initially administered 4 mg mirdametinib twice daily, and wherein the method further comprises one or more of the following:
    (a) upon the patient exhibiting an asymptomatic, absolute decrease in left ventricle ejection fraction (LVEF) of 10% or greater from baseline and is below the lower limit of normal (LLN), withholding the mirdametinib or pharmaceutically acceptable salt thereof until improvement (or, for example, the absolute decrease in LVEF is resolved) and then restarting administration of the mirdametinib or pharmaceutically acceptable salt thereof at a reduced dose;
    (b) upon the patient exhibiting a decrease of 20% or greater in LVEF, permanently discontinuing administration of mirdametinib;
    (c) upon the patient exhibiting a symptomatic retinal pigment epithelium detachment (RPED), withholding the mirdametinib or pharmaceutically acceptable salt thereof until resolution and then restarting administration of the mirdametinib or pharmaceutically acceptable salt thereof at a reduced dose;
    (d) upon the patient exhibiting retinal vein occlusion, permanently discontinuing administration of mirdametinib;
    (e) upon the patient exhibiting a grade 3 or higher dermatitis acneiform or rash, withholding the mirdametinib or pharmaceutically acceptable salt thereof until improvement (or, for example, the dermatitis acneiform is resolved to no higher than a grade 1 dermatitis acneiform or baseline) and then restarting administration of the mirdametinib or pharmaceutically acceptable salt thereof at a reduced dose;
    (f) upon the patient exhibiting any other intolerable grade 2 adverse reaction or any grade 3 adverse reaction, withholding the mirdametinib or pharmaceutically acceptable salt thereof until improvement (or, for example, the adverse reaction is resolved to no higher than grade 1 or baseline) and then restarting administration of mirdametinib or pharmaceutically acceptable salt thereof at a reduced dose; and
    (g) upon the patient exhibiting any grade 4 adverse reaction, withholding the mirdametinib or pharmaceutically acceptable salt thereof until improvement (or, for example, the adverse reaction is resolved to no higher than grade 1 or baseline) and then (x) restarting administration of mirdametinib or pharmaceutically acceptable salt thereof at a reduced dose and (y) optionally considering discontinuing administration of mirdametinib, wherein the reduced dose is:
      (i) upon the patient having a body surface area from 0.4 to 0.69 $m^2$ to reduce the dose from 1 mg twice daily to 1 mg once daily,
      (ii) upon the patient having a body surface area from 0.7 to 1.04 $m^2$ to reduce the dose from 2 mg twice daily to 2 mg in the morning, and 1 mg in the evening,
      (iii) upon the patient having a body surface area from 1.05 to 1.49 $m^2$ to reduce the dose from 3 mg twice daily to 2 mg in the morning and 2 mg in the evening, and
      (iv) upon the patient having a body surface area greater than or equal to 1.5 $m^2$ to reduce the from 4 mg twice daily to 3 mg in the morning and 3 mg in the evening. The initial dosage regimen is continued to be used, unless for instance, an adverse event occurs triggering reduction in the dosage regimen.

The initial dosage regimen is continued to be used, unless for instance, certain adverse events occur which require a reduction in the dosage regimen or discontinuation of treatment with mirdametinib as described herein.

Another aspect is a method of administering mirdametinib or a pharmaceutically acceptable salt thereof to a human patient in need thereof, where the patient suffered from an adverse reaction while being treating with mirdametinib which resolved after withholding the mirdametinib. The method comprising administering to the patient a reduced dose of mirdametinib where the reduced dose is:
  (i) upon the patient having a body surface area from 0.4 to 0.69 $m^2$ to reduce the dose from 1 mg twice daily to 1 mg once daily,
  (ii) upon the patient having a body surface area from 0.7 to 1.04 $m^2$ to reduce the dose from 2 mg twice daily to 2 mg in the morning, and 1 mg in the evening, (iii) upon the patient having a body surface area from 1.05 to 1.49 m² to reduce the dose from 3 mg twice daily to 2 mg in the morning and 2 mg in the evening, and
(iv) upon the patient having a body surface area greater than or equal to 1.5 m² to reduce the from 4 mg twice daily to 3 mg in the morning and 3 mg in the evening.
In one embodiment, prior to withholding the mirdametinib, the patient was administered
(i) for a patient having a body surface area of 0.4 to 0.69 m², 1 mg mirdametinib twice daily,
(ii) for a patient having a body surface area of 0.7 to 1.04 m², 2 mg mirdametinib twice daily,
(iii) for a patient having a body surface area of 1.05 to 1.49 m², 3 mg mirdametinib twice daily, and
(iv) for a patient having a body surface area of at least 1.5 m², 4 mg mirdametinib twice daily. In one embodiment, the adverse reaction was (A) an asymptomatic, absolute decrease in left ventricle ejection fraction (LVEF) of 10% or greater from baseline and is below the lower limit of normal (LLN), (B) a symptomatic retinal pigment epithelium detachment (RPED), (C) a grade 3 or higher dermatitis acneiform or rash, (D) any other intolerable grade 2 adverse reaction or any grade 3 adverse reaction, or (E) any grade 4 adverse reaction.

In one embodiment of any method of any embodiment described herein, the patient suffers from a tumor or cancer. In one embodiment, the tumor or cancer is selected from plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain. In some aspects, the tumor or cancer is high grade glioma. In some aspects, the high grade glioma is a primary cancer. In some aspects, the high grade glioma is a metastatic cancer. In some aspects, the tumor or cancer is low grade ovarian cancer. In some aspects, the tumor or cancer is Langerhans cell histiocytosis. In some aspects, the tumor or cancer is brain cancer. In some aspects, the tumor or cancer is a cancer that has metastasized to the patient's brain including lung cancer, breast cancer and melanoma.

In one embodiment of any of the methods described herein, the patient has plexiform neurofibromas associated with neurofibromatosis type 1 (NF1-PN). In one embodiment, the NF1-PN patient has progressive PN. In one embodiment of any of the methods described herein, the NF1-PN patient has PNs that cause significant morbidity.

In one embodiment of any of the methods described herein, the patient has symptomatic plexiform neurofibromas. In another embodiment of any of the methods described herein, the patient has symptomatic, inoperable plexiform neurofibromas.

In one embodiment of any of the methods described herein, the patient has neurofibromatosis type 1 (NF1) associated plexiform neurofibromas (PN) that is progressing or causing significant morbidity. In one embodiment of any of the methods described herein, the human patient has neurofibromatosis type 1 (NF1) associated inoperable plexiform neurofibromas (PN) that is progressing or causing significant morbidity. In one embodiment, the patient is a pediatric patient. In another embodiment, the patient is an adult.

In one embodiment of any of the methods described herein, the administration of mirdametinib results in decreased pain intensity.

In one embodiment of any of the methods described herein, the administration of mirdametinib results in decreased pain interference.

Yet another embodiment is a method of treating an adult or pediatric human patient at least 2 years of age having neurofibromatosis type 1 (NF1) who has symptomatic plexiform neurofibromas (PN) and is in need thereof by orally administering to the patient mirdametinib or a pharmaceutically acceptable salt thereof, wherein
(i) for a patient having a body surface area of 0.4 to 0.69 m², the patient is initially administered 1 mg mirdametinib twice daily,
(ii) for a patient having a body surface area of 0.7 to 1.04 m², the patient is initially administered 2 mg mirdametinib twice daily,
(iii) for a patient having a body surface area of 1.05 to 1.49 m², the patient is initially administered 3 mg mirdametinib twice daily, and
(iv) for a patient having a body surface area of at least 1.5 m², the patient is initially administered 4 mg mirdametinib twice daily, and wherein the method further comprises one or more of the following:
(a) upon the patient exhibiting an asymptomatic, absolute decrease in left ventricle ejection fraction (LVEF) 10% or greater from baseline and is below the lower limit of normal (LLN), withholding the mirdametinib or pharmaceutically acceptable salt thereof until improvement (or, for example, the absolute decrease in LVEF is resolved) and then restarting administration of the mirdametinib or pharmaceutically acceptable salt thereof at a reduced dose;
(b) upon the patient exhibiting a decrease of 20% or greater in LVEF, permanently discontinuing administration of mirdametinib;
(c) upon the patient exhibiting a symptomatic retinal pigment epithelium detachment (RPED), withholding the mirdametinib or pharmaceutically acceptable salt thereof until resolution and then restarting administration of the mirdametinib or pharmaceutically acceptable salt thereof at a reduced dose;
(d) upon the patient exhibiting retinal vein occlusion, permanently discontinuing administration of mirdametinib;
(e) upon the patient exhibiting a grade 3 or higher dermatitis acneiform or rash, withholding the mirdametinib or pharmaceutically acceptable salt thereof until improvement (or, for example, the dermatitis acneiform is resolved to no higher than a grade 1 dermatitis acneiform or baseline) and then restarting administration of the mirdametinib or pharmaceutically acceptable salt thereof at a reduced dose;
(f) upon the patient exhibiting any other intolerable grade 2 adverse reaction or any grade 3 adverse reaction, withholding the mirdametinib or pharmaceutically acceptable salt thereof until improvement (or, for example, the adverse reaction is resolved to no higher than grade 1 or baseline) and then restarting administration of mirdametinib or pharmaceutically acceptable salt thereof at a reduced dose; and
(g) upon the patient exhibiting any grade 4 adverse reaction, withholding the mirdametinib or pharmaceutically acceptable salt thereof until improvement (or, for example, the adverse reaction is resolved to no higher than grade 1 or baseline) and then (x) restarting administration of mirdametinib or pharmaceutically acceptable salt thereof at a reduced dose and (y) optionally considering discontinuing administration of mirdametinib, wherein the reduced dose is:
  (i) upon the patient having a body surface area from 0.4 to 0.69 m² to reduce the dose from 1 mg twice daily to 1 mg once daily,
  (ii) upon the patient having a body surface area from 0.7 to 1.04 m² to reduce the dose from 2 mg twice daily to 2 mg in the morning, and 1 mg in the evening,
  (iii) upon the patient having a body surface area from 1.05 to 1.49 m² to reduce the dose from 3 mg twice daily to 2 mg in the morning and 2 mg in the evening, and
  (iv) upon the patient having a body surface area greater than or equal to 1.5 m² to reduce the from 4 mg twice daily to 3 mg in the morning and 3 mg in the evening.

In one embodiment of any method of any embodiment described herein, (a) upon the patient exhibiting an asymptomatic, absolute decrease in left ventricle ejection fraction (LVEF) of 10% or greater and no more than 20% from baseline and is below the lower limit of normal (LLN), withholding the mirdametinib or pharmaceutically acceptable salt thereof until the absolute decrease in LVEF is resolved and then restarting administration of the mirdametinib or pharmaceutically acceptable salt thereof at the reduced dose.

In one embodiment of any method of any embodiment described herein, the adverse reaction in (f) or (g) is selected from diarrhea, abdominal pain, and fatigue.

In one embodiment of any method of any embodiment described herein, (g) upon the patient exhibiting any grade 4 adverse reaction, permanently discontinuing administration of mirdametinib.

Yet another embodiment is a method of treating an adult or pediatric human patient at least 2 years of age having neurofibromatosis type 1 (NF1) who has symptomatic plexiform neurofibromas (PN) and is in need thereof, where the patient suffered from an adverse reaction while being treating with mirdametinib which resolved after withholding the mirdametinib. The method comprising administering to the patient a reduced dose of mirdametinib where the reduced dose is:
  (i) upon the patient having a body surface area from 0.4 to 0.69 m² to reduce the dose from 1 mg twice daily to 1 mg once daily,
  (ii) upon the patient having a body surface area from 0.7 to 1.04 m² to reduce the dose from 2 mg twice daily to 2 mg in the morning, and 1 mg in the evening,
  (iii) upon the patient having a body surface area from 1.05 to 1.49 m² to reduce the dose from 3 mg twice daily to 2 mg in the morning and 2 mg in the evening, and
  (iv) upon the patient having a body surface area greater than or equal to 1.5 m² to reduce the from 4 mg twice daily to 3 mg in the morning and 3 mg in the evening. In one embodiment, prior to withholding the mirdametinib, the patient was administered
  (i) for a patient having a body surface area of 0.4 to 0.69 m², 1 mg mirdametinib twice daily,
  (ii) for a patient having a body surface area of 0.7 to 1.04 m², 2 mg mirdametinib twice daily,
  (iii) for a patient having a body surface area of 1.05 to 1.49 m², 3 mg mirdametinib twice daily, and
  (iv) for a patient having a body surface area of at least 1.5 m², 4 mg mirdametinib twice daily. In one embodiment, the adverse reaction was (A) an asymptomatic, absolute decrease in left ventricle ejection fraction (LVEF) of 10% or greater from baseline and is below the lower limit of normal (LLN), (B) a symptomatic retinal pigment epithelium detachment (RPED), (C) a grade 3 or higher dermatitis acneiform or rash, (D) any other intolerable grade 2 adverse reaction or any grade 3 adverse reaction, or (E) any grade 4 adverse reaction.

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient an effective amount of mirdametinib or a pharmaceutically acceptable salt thereof, wherein (i) the patient exhibits, at steady state exposure from administration of mirdametinib or a pharmaceutically acceptable salt thereof, a $C_{max}$ of mirdametinib of from about 95 to about 280 ng/mL and (ii) upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering
  (i) for a patient having a body surface area from 0.4 to 0.69 m², 1 mg once daily,
  (ii) for a patient having a body surface area from 0.7 to 1.04 m², 2 mg in the morning, and 1 mg in the evening,
  (iii) for a patient having a body surface area from 1.05 to 1.49 m², 2 mg in the morning and 2 mg in the evening, and
  (iv) for a patient having a body surface area greater than or equal to 1.5 m², 3 mg in the morning and 3 mg in the evening.

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient an effective amount of mirdametinib or a pharmaceutically acceptable salt thereof, wherein
  (a) the patient exhibits, at steady state exposure from administration of mirdametinib or a pharmaceutically acceptable salt thereof, a $C_{max}$ of mirdametinib of from about 95 to about 280 ng/ml and
  (b) upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then restarting administration of the mirdametinib or pharmaceutically acceptable salt thereof at a reduced dose;
  (c) upon the patient exhibiting a decrease of 20% or greater in LVEF, permanently discontinuing administration of mirdametinib;
  (d) upon the patient exhibiting a symptomatic retinal pigment epithelium detachment (RPED), withholding the mirdametinib or pharmaceutically acceptable salt thereof until resolution and then restarting administration of the mirdametinib or pharmaceutically acceptable salt thereof at a reduced dose;
  (e) upon the patient exhibiting retinal vein occlusion, permanently discontinuing administration of mirdametinib;
  (f) upon the patient exhibiting a grade 3 or higher dermatitis acneiform or rash, withholding the mirdametinib or pharmaceutically acceptable salt thereof until improvement and then restarting administration of the mirdametinib or pharmaceutically acceptable salt thereof at a reduced dose;

(g) upon the patient exhibiting any other intolerable grade 2 or grade 3 adverse reaction, withholding the mirdametinib or pharmaceutically acceptable salt thereof until improvement and then restarting administration of mirdametinib or pharmaceutically acceptable salt thereof at a reduced dose; and (h) upon the patient exhibiting any other grade 4 adverse reaction, withholding the mirdametinib or pharmaceutically acceptable salt thereof until improvement and then (x) restarting administration of mirdametinib or pharmaceutically acceptable salt thereof at a reduced dose, wherein the reduced dose is:
  (i) for a patient having a body surface area from 0.4 to 0.69 m$^2$, 1 mg once daily,
  (ii) for a patient having a body surface area from 0.7 to 1.04 m$^2$, 2 mg in the morning, and 1 mg in the evening,
  (iii) for a patient having a body surface area from 1.05 to 1.49 m$^2$, 2 mg in the morning and 2 mg in the evening, and
  (iv) for a patient having a body surface area greater than or equal to 1.5 m$^2$, 3 mg in the morning and 3 mg in the evening.

Yet another embodiment is a method of treating an adult or pediatric patient at least 2 years of age having neurofibromatosis type 1 (NF1) who has symptomatic plexiform neurofibromas (PN) and is in need thereof, the method comprising orally administering to the patient mirdametinib or a pharmaceutically acceptable salt thereof, wherein (i) the patient exhibits, at steady state exposure from administration of mirdametinib or a pharmaceutically acceptable salt thereof, an AUC$_{last}$ of mirdametinib of from about 200 to about 720 ng h/mL, and (ii) upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering
  (i) for a patient having a body surface area from 0.4 to 0.69 m$^2$, 1 mg once daily,
  (ii) for a patient having a body surface area from 0.7 to 1.04 m$^2$, 2 mg in the morning, and 1 mg in the evening,
  (iii) for a patient having a body surface area from 1.05 to 1.49 m$^2$, 2 mg in the morning and 2 mg in the evening, and
  (iv) for a patient having a body surface area greater than or equal to 1.5 m$^2$, 3 mg in the morning and 3 mg in the evening.

Yet another embodiment is a method of treating a patient at least 2 years of age having neurofibromatosis type 1 (NF1) who has symptomatic plexiform neurofibromas (PN) and is in need thereof, the method comprising orally administering to the patient a daily dose of 2 mg of mirdametinib or a pharmaceutically acceptable salt thereof, wherein upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient a reduced daily dose of 1 mg of mirdametinib or the pharmaceutically acceptable salt thereof. The 2 mg daily dose can be administered to the patient as, for example, two 1 mg dosages of mirdametinib or a pharmaceutically acceptable salt thereof. The 1 mg reduced daily dose can administered to the patient, for example, once daily.

Yet another embodiment is a method of treating a patient at least 2 years of age having neurofibromatosis type 1 (NF1) who has symptomatic plexiform neurofibromas (PN) and is in need thereof, the method comprising orally administering to the patient a daily dose of 4 mg of mirdametinib or a pharmaceutically acceptable salt thereof, wherein upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient a reduced daily dose of 3 mg of mirdametinib or the pharmaceutically acceptable salt thereof. The 4 mg daily dose can be administered to the patient as, for example, two 2 mg dosages of mirdametinib or a pharmaceutically acceptable salt thereof. The 3 mg reduced daily dose can administered to the patient, for example, as a 2 mg dosage in the morning and a 1 mg dosage in the evening.

Yet another embodiment is a method of treating a patient at least 2 years of age having neurofibromatosis type 1 (NF1) who has symptomatic plexiform neurofibromas (PN) and is in need thereof, the method comprising orally administering to the patient a daily dose of 6 mg of mirdametinib or a pharmaceutically acceptable salt thereof, wherein upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient a reduced daily dose of 4 mg of mirdametinib or the pharmaceutically acceptable salt thereof. The 6 mg daily dose can be administered to the patient as, for example, two 3 mg dosages of mirdametinib or a pharmaceutically acceptable salt thereof. The 4 mg reduced daily dose can administered to the patient, for example, as a 2 mg dosage in the morning and a 2 mg dosage in the evening.

Yet another embodiment is a method of treating a patient at least 2 years of age having neurofibromatosis type 1 (NF1) who has symptomatic plexiform neurofibromas (PN) and is in need thereof, the method comprising orally administering to the patient a daily dose of 8 mg of mirdametinib or a pharmaceutically acceptable salt thereof, wherein upon the patient exhibiting an asymptomatic, absolute decrease in left ventricle ejection fraction (LVEF) 10% or greater from baseline and is below the lower limit of normal (LLN), withholding mirdametinib or a pharmaceutically acceptable salt thereof until improvement of the LVEF and then administering to the patient a reduced daily dose of 6 mg of mirdametinib or the pharmaceutically acceptable salt thereof. The 8 mg daily dose can be administered to the patient as, for example, two 4 mg dosages of mirdametinib or a pharmaceutically acceptable salt thereof. The 6 mg reduced daily dose can administered to the patient, for example, as a 3 mg dosage in the morning and a 3 mg dosage in the evening.

Yet another embodiment is a method of treating a patient at least 2 years of age having a tumor or cancer and in need thereof, the method comprising orally administering to the patient mirdametinib or a pharmaceutically acceptable salt thereof, wherein upon the patient exhibiting a symptomatic retinal pigment epithelium detachment (RPED), withholding the mirdametinib or pharmaceutically acceptable salt thereof until resolution and then administering the mirdametinib or pharmaceutically acceptable salt thereof at a reduced dose, wherein the reduced dose is:
   (i) for a patient having a body surface area from 0.4 to 0.69 m², 1 mg once daily,
   (ii) for a patient having a body surface area from 0.7 to 1.04 m², 2 mg in the morning, and 1 mg in the evening,
   (iii) for a patient having a body surface area from 1.05 to 1.49 m², 2 mg in the morning and 2 mg in the evening, and
   (iv) for a patient having a body surface area greater than or equal to 1.5 m², 3 mg in the morning and 3 mg in the evening. In some instances, upon the patient exhibiting retinal vein occlusion, the method comprises permanently discontinuing administration of mirdametinib. In some instances, is the patient exhibits an asymptomatic, absolute decrease in left ventricle ejection fraction (LVEF) of 10% or greater from baseline and is below the lower limit of normal (LLN), the method may further comprise withholding the mirdametinib or pharmaceutically acceptable salt thereof until improvement and then restarting administration of the mirdametinib or pharmaceutically acceptable salt thereof at the reduced dose. In some instances, the patient exhibits an asymptomatic, absolute decrease in LVEF of 10% or greater and no more than 20% from baseline and is below the LLN. In some instances, the patient exhibits, at steady state exposure from administration of mirdametinib or a pharmaceutically acceptable salt thereof, a $AUC_{last}$ of mirdametinib of from about 200 to about 720 ng h/mL, prior to the patient exhibiting a symptomatic RPED. In some instances, the patient exhibits, at steady state exposure from administration of mirdametinib or a pharmaceutically acceptable salt thereof, a $C_{max}$ of mirdametinib of from about 95 to about 280 ng/mL, prior to the patient exhibiting a symptomatic RPED.

Yet another embodiment is a method of treating a patient at least 2 years of age having neurofibromatosis type 1 (NF1) who has symptomatic plexiform neurofibromas (PN), the method comprising orally administering to the patient mirdametinib or a pharmaceutically acceptable salt thereof, wherein
   (i) for a patient having a body surface area of 0.4 to 0.69 m², the patient is initially administered 1 mg mirdametinib twice daily,
   (ii) for a patient having a body surface area of 0.7 to 1.04 m², the patient is initially administered 2 mg mirdametinib twice daily,
   (iii) for a patient having a body surface area of 1.05 to 1.49 m², the patient is initially administered 3 mg mirdametinib twice daily, and
   (iv) for a patient having a body surface area of at least 1.5 m², the patient is initially administered 4 mg mirdametinib twice daily, and
wherein upon the patient exhibiting a symptomatic retinal pigment epithelium detachment (RPED), withholding the mirdametinib or pharmaceutically acceptable salt thereof until resolution and then administering the mirdametinib or pharmaceutically acceptable salt thereof at a reduced dose, wherein the reduced dose is:
   (I) for a patient having a body surface area from 0.4 to 0.69 m², 1 mg once daily,
   (II) for a patient having a body surface area from 0.7 to 1.04 m², 2 mg in the morning, and 1 mg in the evening,
   (III) for a patient having a body surface area from 1.05 to 1.49 m², 2 mg in the morning and 2 mg in the evening, and
   (IV) for a patient having a body surface area greater than or equal to 1.5 m², 3 mg in the morning and 3 mg in the evening. In some instances, upon the patient exhibiting retinal vein occlusion, the method comprises permanently discontinuing administration of mirdametinib. In some instances, is the patient exhibits an asymptomatic, absolute decrease in left ventricle ejection fraction (LVEF) of 10% or greater from baseline and is below the lower limit of normal (LLN), the method may further comprise withholding the mirdametinib or pharmaceutically acceptable salt thereof until improvement and then restarting administration of the mirdametinib or pharmaceutically acceptable salt thereof at the reduced dose. In some instances, the patient exhibits an asymptomatic, absolute decrease in LVEF of 10% or greater and no more than 20% from baseline and is below the LLN. In some instances, the patient exhibits, at steady state exposure from administration of mirdametinib or a pharmaceutically acceptable salt thereof, a $AUC_{last}$ of mirdametinib of from about 200 to about 720 ng h/mL, prior to the patient exhibiting a symptomatic RPED. In some instances, the patient exhibits, at steady state exposure from administration of mirdametinib or a pharmaceutically acceptable salt thereof, a $C_{max}$ of mirdametinib of from about 95 to about 280 ng/ml, prior to the patient exhibiting a symptomatic RPED.

In one embodiment of any method of any embodiment described herein, the mirdametinib or pharmaceutically acceptable salt thereof is administered with or without food.

In one embodiment of any method of any embodiment described herein, if a patient misses a dose of mirdametinib, the patient skips that dose and resumes administration at the next scheduled dose.

In one embodiment of any method of any embodiment described herein, if vomiting occurs after administering a dose of mirdametinib, the patient does not administer an additional dose of mirdametinib, but continues with administration at the next scheduled dose.

In some embodiments directed towards any of the methods described herein, wherein the patient is an adult patient having neurofibromatosis type 1 (NF1) who has symptomatic plexiform neurofibromas (PN).

In some embodiments directed towards any of the methods described herein, wherein the patient is a pediatric patient having neurofibromatosis type 1 (NF1) who has symptomatic plexiform neurofibromas (PN).

In some embodiments directed towards any of the methods described herein, wherein the mirdametinib or pharmaceutically acceptable salt thereof is administered for the first 21 days or each 28-day cycle.

In some embodiments directed towards any of the methods described herein, wherein the mirdametinib or pharmaceutically acceptable salt thereof is administered until plexiform neurofibromas progression or unacceptable toxicity.

In one embodiment of any of the methods described herein, the treatment results in decreased pain intensity.

In one embodiment of any of the methods described herein, the treatment results in decreased pain interference.

In one embodiment of any method of any embodiment described herein, the patient is an adult patient having neurofibromatosis type 1 (NF1) who has symptomatic plexiform neurofibromas (PN).

In one embodiment of any method of any embodiment described herein, the patient is a pediatric patient having neurofibromatosis type 1 (NF1) who has symptomatic plexiform neurofibromas (PN).

In one embodiment of any method of any embodiment described herein, the mirdametinib or pharmaceutically acceptable salt thereof is administered for the first 21 days of each 28-day cycle.

In one embodiment of any method of any embodiment described herein, the mirdametinib or pharmaceutically acceptable salt thereof is administered until plexiform neurofibromas progression or unacceptable toxicity.

In one embodiment of any method of any embodiment described herein, the left ventricle ejection fraction (LVEF) is assessed by echocardiogram prior to initiating treatment with mirdametinib and every 3 months during the first year of treatment with mirdametinib.

In one embodiment of any method of any embodiment described herein, a comprehensive ophthalmic assessment is conducted prior to initiating treatment with mirdametinib and at regular intervals during treatment with mirdametinib, and for new or worsening visual changes.

In one embodiment of any method of any embodiment described herein, the patient has symptomatic, inoperable plexiform neurofibromas.

In one embodiment of any method of any embodiment described herein, the patient has progressive plexiform neurofibromas.

In one embodiment of any method of any embodiment described herein, the patient has plexiform neurofibromas that cause significant morbidity.

In one embodiment of any method of any embodiment described herein, the NF1-PN patient has head and neck lesions that are compromising the airway or great vessels, brachial or lumbar plexus lesions that are causing nerve compression and loss of function, lesions causing major deformity or are significantly disfiguring, lesions of the extremity that cause limb hypertrophy or loss of function or painful lesions. In one embodiment, the lesions causing major deformity or are significantly disfiguring are tumors of the head and neck or those on other areas of the body that are unable to be concealed by standard garments. In one embodiment of any method of any embodiment described herein, the patient has paraspinal lesions.

In one embodiment of any of the methods described herein, the patient has the clinical diagnosis of NF1 using the NIH Consensus Conference and one or more of the following:
(a) six or more café-au-lait macules with a diameter >5 mm in prepubertal and >15 mm in post-pubertal individuals;
(b) freckling in axilla or inguinal regions;
(c) optic glioma;
(d) two or more Lisch nodules;
(e) a distinctive bony lesion (dysplasia of the sphenoid bone or dysplasia of thinning of long bone cortex); and
(f) a first degree relative with NF1.

In one embodiment of any of the methods described herein, the patient has a constitutional NF1 mutation documented in a Clinical Laboratory Improvement Amendments/College of American Pathologists certified lab.

In one embodiment of any of the methods described herein, the patient either (a) has a parent diagnosed with NF1 and one or more criteria of (1) through (7) or (b) does not have a parent diagnosed with NF1 but has two or more criteria of (1) through (7):

(1) six or more café-au-lait macules over 5 mm in greatest diameter in prepubertal individuals and over 15 mm in greatest diameter in post-pubertal individuals;
(2) freckling in the axillary or inguinal region;
(3) two or more neurofibromas of any type or one plexiform neurofibroma
(4) optic pathway glioma;
(5) two or more iris Lisch nodules identified by slit lamp examination or two or more choroidal abnormalities (defined as bright, patchy nodules imaged by optical coherence tomography (OCT)/near-infrared reflectance (NIR) imaging;
(6) a distinctive osseous lesion (such as sphenoid dysplasia, anterolateral bowing of the tibia, or pseudarthrosis of a long bone); and
(7) a heterozygous pathogenic NF1 variant with a variant allele fraction of 50% in apparently normal tissue such as white blood cells.

In one embodiment of any of the methods described herein, over each four week period, the mirdametinib is administered for the first three weeks and discontinued for the last one week.

In one embodiment, the adverse event resulting in the dose reduction is acneiform. In another embodiment, the adverse event resulting in the dose reduction is dermatitis acneiform. In yet another embodiment, the adverse event resulting in the dose reduction is dermatitis acneiform, diarrhea, or nausea. In yet another embodiment, the adverse event resulting in the dose reduction in a pediatric patient is decreased neutrophil count.

In one embodiment of any of the methods described herein, the patient has at least a 20% reduction in plexiform neurofibroma volume as determined by volumetric magnetic resonance imaging analysis following treatment with mirdametinib.

In one embodiment of any of the methods described herein, the patient permanently discontinues treatment with mirdametinib due to a grade 4 adverse reaction where the adverse reaction is abdominal pain, constipation, dermatitis acneiform, or diarrhea. In one embodiment of any of the methods described herein, the pediatric patient permanently discontinues treatment with mirdametinib due to a grade 4 adverse reaction where the adverse reaction is abdominal pain, constipation, dermatitis acneiform, or diarrhea.

In one embodiment of any method of any embodiment described herein, the patient exhibits, at steady state exposure from administration of mirdametinib or a pharmaceutically acceptable salt thereof, a $C_{max}$ of mirdametinib from about 100 ng/ml to about 500 ng/ml. In one embodiment, the patient exhibits, at steady state exposure from administration of mirdametinib or a pharmaceutically acceptable salt thereof, a $C_{max}$ of mirdametinib of from about 95 to about 280 ng/ml (such as from about 130 to about 245, from about 150 to about 230, or from about 160 to about 215 ng/ml), prior to withholding the mirdametinib or pharmaceutically acceptable salt thereof.

In one embodiment of any method of any embodiment described herein, the patient exhibits, at steady state exposure from administration of mirdametinib or a pharmaceutically acceptable salt thereof, a $AUC_{last}$ of mirdametinib of from about 200 to about 720 ng·h/mL (such as from about 250 to about 610, from about 250 to about 670, from about 350 to about 510, from about 350 to about 660, from about 380 to about 700, from about 380 to about 480, or from about 410 to about 510 ng h/mL), prior to withholding the mirdametinib or pharmaceutically acceptable salt thereof.

In one embodiment of any of the methods described herein, the patient is 2 to 15 years of age.

In one embodiment of any of the methods described herein, the method further comprises prior to treatment (i) determining whether to select mirdametinib as a treatment for the patient, and (ii) selecting mirdametinib as a treatment for the patient at least partially based on its objective response rate, where the objective response rate is defined as at least a 20% decrease in tumor size using centrally read MRI volumetric analysis (for example, per Response Evaluation in Neurofibromatosis and Schwannomatosis (REINS) criteria). In one embodiment, in step (i), mirdametinib is selected based on a response rate of at least 40% in adult patients, such as an objective response rate of 41%. In another embodiment, in step (i), mirdametinib is selected based on a response rate of at least 50% in pediatric patients, such as an objective response rate of 52%.

Methods for treating a tumor or cancer selected from the group consisting of plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain, comprising administering to a patient in need thereof mirdametinib or a pharmaceutically acceptable salt thereof are also provided herein. The mirdametinib or a pharmaceutically acceptable salt thereof may be administered according to the dosing scheme described herein.

In one embodiment of any of the methods described herein, wherein the maximum daily dose is 4 mg mirdametinib twice daily.

In one embodiment of any of the methods described herein, over each four week period, the mirdametinib is administered for the first three weeks and discontinued for the last one week.

In one embodiment of any of the methods described herein, the patient has at least a 20% reduction in plexiform neurofibroma volume as determined by volumetric magnetic resonance imaging analysis following treatment with mirdametinib.

In one embodiment of any of the methods described herein, the treatment or administration of mirdametinib results in decreased pain intensity.

In one embodiment of any of the methods described herein, the treatment or administration of mirdametinib results in decreased pain interference.

In one embodiment of any of the methods described herein, the dose administered is reduced due to an adverse event, wherein the dose is reduced as follows:
 (a) if the dose at the time of the event is 1 mg mirdametinib twice daily, then the reduced daily dose is 1 mg administered in the morning only;
 (b) if the dose at the time of the event is 2 mg mirdametinib twice daily, then the reduced daily dose is 2 mg administered in the morning and 1 mg administered in the evening;
 (c) if the dose at the time of the event is 3 mg mirdametinib twice daily, then the reduced daily dose is 2 mg administered twice daily; and
 (d) if the dose at the time of the event is 4 mg mirdametinib twice daily, then the reduced daily dose is 3 mg administered twice daily. In one embodiment, the adverse event resulting in the dose reduction is acneiform.

In one embodiment of any of the methods described herein, the patient is 2 to 15 years of age.

In one embodiment of any of the methods described herein, the method further comprises prior to treatment (i) determining whether to select mirdametinib as a treatment for the patient, and (ii) selecting mirdametinib as a treatment for the patient at least partially based on its objective response rate, where the objective response rate is defined as at least a 20% decrease in tumor size using centrally read MRI volumetric analysis. In one embodiment, in step (i), mirdametinib is selected based on a response rate of at least 40% in adult patients, such as an objective response rate of 41%. In another embodiment, in step (i), mirdametinib is selected based on a response rate of at least 50% in pediatric patients, such as an objective response rate of 52%.

In some aspects, a therapeutically effective amount of mirdametinib, or a pharmaceutically acceptable salt thereof, is administered.

In some aspects, the mirdametinib, or a pharmaceutically acceptable salt thereof, is administered as mirdametinib free base.

In some aspects, the mirdametinib, or a pharmaceutically acceptable salt thereof, exhibits high blood-brain-barrier penetration.

In some aspects, the patient is a human.

In some aspects, the human patient has an age of ≥2 and <25 years. In some aspects, the human has an age of ≥2 and 18 years.

In some aspects, the human patient has had no prior exposure to MEK inhibitors. In some aspects, the human patient has not responded to prior treatment to one or more MEK inhibitors.

In some aspects, the mirdametinib, or a pharmaceutically acceptable salt thereof, is administered orally. In some aspects, the mirdametinib, or a pharmaceutically acceptable salt thereof, is administered orally as a solid dosage form. In some aspects, the solid dosage form is a tablet or capsule. In some aspects, the solid dosage form is a capsule. In some aspects, the mirdametinib, or a pharmaceutically acceptable salt thereof, is dispersible in a potable liquid (e.g., about 5 to about 10 mL of water) or orodispersible in a patient's saliva. In one embodiment, the mirdametinib, or a pharmaceutically acceptable salt thereof, is administered as a dispersible formulation (such as a 0.5 mg or 1 mg mirdametinib dispersible tablet) as described in U.S. Pat. No. 11,571,402, which is hereby incorporated by reference. In one embodiment, prior to oral administration, a tablet of mirdametinib (such as a 1 mg tablet) is added to about 5 to about 10 mL of water and then gently swirled to disperse the tablet until no lumps remain. The oral solution is subsequently administered to a patient.

In some aspects, the mirdametinib, or a pharmaceutically acceptable salt thereof, is administered as a monotherapy to treat the tumor or cancer.

In some aspects, the mirdametinib, or a pharmaceutically acceptable salt thereof, is administered in combination with another active ingredient and/or surgery to treat the tumor or cancer.

In some embodiments of the present invention, the adverse event resulting in a dose reduction is a laboratory abnormality. In some instances, the laboratory abnormality is increased blood creatine phosphokinase. In some instances, the laboratory abnormality is increased aspartate aminotransferase (AST). In some instances, the laboratory abnormality is increased alanine aminotransferase (ALT). In some instances, the laboratory abnormality is increased blood alkaline phosphatase. In some instances, the laboratory abnormality is decreased neutrophil count.

In one embodiment of any of the methods described herein, the patient exhibits, at steady state exposure from administration of mirdametinib or a pharmaceutically acceptable salt thereof, a $C_{max}$ of mirdametinib from about 100 ng/ml to about 500 ng/ml, prior to withholding the mirdametinib or pharmaceutically acceptable salt thereof.

In another embodiment of any of the methods described herein, the patient exhibits, at steady state exposure from administration of mirdametinib or a pharmaceutically acceptable salt thereof, a $C_{max}$ of mirdametinib of from about 95 to about 280 ng/ml (such as from about 130 to about 245, from about 150 to about 230, or from about 160 to about 215 ng/mL), prior to withholding the mirdametinib or pharmaceutically acceptable salt thereof.

In another embodiment of any of the methods described herein, the patient exhibits, at steady state exposure from administration of mirdametinib or a pharmaceutically acceptable salt thereof, a $AUC_{last}$ of mirdametinib of from about 200 to about 720 ng·h/mL (such as from about 250 to about 610, from about 250 to about 670, from about 350 to about 510, from about 350 to about 660, from about 380 to about 700, from about 380 to about 480, or from about 410 to about 510 ng h/mL), prior to withholding the mirdametinib or pharmaceutically acceptable salt thereof.

Iii. Dosage Forms

The mirdametinib in the methods described herein may be orally administered in the form of an oral dosage form (such as a tablet or capsule). In one embodiment, the oral dosage form comprises (a) mirdametinib having a d90 no more than 250 microns and (b) one or more pharmaceutically acceptable excipients. In one embodiment, the mirdametinib has a d90 ranging from 50 to 150 microns. In another embodiment, the mirdametinib has a d90 ranging from 150 to 250 microns. In yet another embodiment, the mirdametinib has a d50 of no more than 50 microns. In yet another embodiment, the mirdametinib has a d50 of 1 to 25 microns. In yet another embodiment, the mirdametinib has a d50 of 25 to 50 microns. In yet another embodiment, the mirdametinib has a d50 of no more than 30 microns. The oral dosage form may be a solid oral dosage form, such as a capsule or tablet (e.g., dispersible tablet). In one embodiment, the oral dosage form contains 1 mg mirdametinib. In another embodiment, the oral dosage form contains 2 mg mirdametinib.

In another embodiment, the oral dosage form comprises (a) mirdametinib having a d50 no more than 50 microns and (b) one or more pharmaceutically acceptable excipients. In one embodiment, the mirdametinib has a d50 of 1 to 25 microns. In yet another embodiment, the mirdametinib has a d50 of 25 to 50 microns. In yet another embodiment, the mirdametinib has a d50 of no more than 30 microns. The oral dosage form may be a solid oral dosage form, such as a capsule or tablet (e.g., dispersible tablet). In one embodiment, the oral dosage form contains 1 mg mirdametinib. In another embodiment, the oral dosage form contains 2 mg mirdametinib.

In one embodiment, the oral dosage form is a capsule prepared by (i) roller compaction of a blend of the mirdametinib and one or more pharmaceutically acceptable excipients and (ii) encapsulating the compacted blend into a capsule.

In yet another embodiment, the oral dosage form comprises (a) 1 mg mirdametinib having a d90 no more than 250 microns and (b) one or more pharmaceutically acceptable excipients, wherein the dosage form provides upon oral administration, on the first day of treatment with mirdametinib, an $AUC_{0-12h}$ less than 400 ng·h/mL, a $C_{max}$ no more than 40 ng/ml, or both. In one embodiment, the dosage form provides upon oral administration, on the first day of treatment with mirdametinib, an $AUC_{0-12h}$ less than 200 ng·h/mL. In another embodiment, the dosage form provides upon oral administration, on the first day of treatment with mirdametinib, $AUC_{0-12h}$ less than 100 ng·h/mL. In yet another embodiment, the dosage form provides upon oral administration, on the first day of treatment with mirdametinib, a $C_{max}$ no more than 32 ng/ml. In yet another embodiment, the dosage form provides upon oral administration, on the first day of treatment with mirdametinib, a $C_{max}$ no more than 30 ng/mL.

Yet another aspect is an oral dosage form comprising (a) 1 mg mirdametinib having a d50 no more than 50 microns and (b) one or more pharmaceutically acceptable excipients, wherein the dosage form provides upon oral administration, on the first day of treatment with mirdametinib, an $AUC_{0-12h}$ less than 400 ng h/mL, a $C_{max}$ no more than 40 ng/mL, or both. In one embodiment, the dosage form provides upon oral administration, on the first day of treatment with mirdametinib, an $AUC_{0-12h}$ less than 200 ng·h/mL. In another embodiment, the dosage form provides upon oral administration, on the first day of treatment with mirdametinib, $AUC_{0-12h}$ less than 100 ng·h/mL. In yet another embodiment, the dosage form provides upon oral administration, on the first day of treatment with mirdametinib, a $C_{max}$ no more than 32 ng/ml. In yet another embodiment, the dosage form provides upon oral administration, on the first day of treatment with mirdametinib, a $C_{max}$ no more than 30 ng/mL.

In one embodiment, the oral dosage form of any embodiment described herein releases at least 80% of its mirdametinib within 15 minutes as measured according to the USP basket method in 0.1 N HCl (0.1 N HCL aqueous solution) and at 75 rpm.

EXAMPLE

Example 1: Phase 2b Trial of Mirdametinib in Adult and Pediatric Patients with Neurofibromatosis Type 1 (NF1)-Associated Inoperable Plexiform Neurofibromas (PNs) that are Progressing or Causing Significant Morbidity This study is to evaluate the efficacy, safety, and tolerability of mirdametinib in participants ≥2 years of age with symptomatic NF1-associated plexiform neurofibromas (PNs) that causes significant morbidity.

Participants were screened (assessed for eligibility as described below). A total of 58 adult patients received mirdametinib. The median age was 34.5 years (range 18 to 69 years); 85% were white and 64% were female. Approximately half of the patients (53%) had a progressing PN at study entry. The most commonly reported morbidities were pain (90%) and disfigurement or major deformity (52%).

A total of 56 pediatric patients received mirdametinib. The median age was 10 years (range 2 to 17 years); 66% were white and 54% were female. Most patients (63%) had a progressing PN at study entry. The most commonly reported morbidities were pain (70%) and disfigurement or major deformity (50%).

Participants were screened for up to 28 days prior to the first dose of study treatment mirdametinib. Study treatment was administered orally at a twice daily (BID) dose specified in the table below. Dosing was on a 28-day Cycle (4-week course) with a 3 week on/1 week off schedule. The treatment period will last for up to 24 Cycles followed by a 30-day Safety Follow-Up period.

| Subject's BSA (m$^2$) | ≤0.69 | 0.7 to 1.04 | 1.05 to 1.49 | ≥1.5 |
|---|---|---|---|---|
| BID dose (mg) | 1 | 2 | 3 | 4 |

A partial response was defined as PN decrease ≥20% compared to baseline using centrally read MRI volumetric analysis.

Inclusion Criteria

Patients are eligible to be included in the study only if all of the following criteria apply:
1. Participant must be >2 years of age inclusive, at the time of signing the informed consent/assent.
2. Participants must have either the clinical diagnosis of NF1 using the National Institute of Health (NIH) Consensus Conference criteria of at least 1 other diagnostic criterion (Inclusion 2.1-2.6, see below) in addition to the presence of PN, or have a constitutional NF1 mutation documented in a Clinical Laboratory Improvement Amendments/College of American Pathologists certified lab; additional criteria are as follows:
    2.1. Six or more café-au-lait macules with a diameter >5 mm in prepubertal and >15 mm in post-pubertal individuals, respectively 2.2. Freckling in axilla or inguinal regions;
    2.3. Optic glioma;
    2.4. Two or more Lisch nodules;
    2.5. A distinctive bony lesion (dysplasia of the sphenoid bone or dysplasia of thinning of long bone cortex);
    2.6. A first degree relative with NF1.
3. Participants must have PN that is progressive (Inclusion 3.1) OR causing significant morbidity, such as (but not limited to) head and neck lesions that are compromising the airway or great vessels, brachial or lumbar plexus lesions that are causing nerve compression and loss of function, lesions causing major deformity or are significantly disfiguring (Inclusion 3.2), lesions of the extremity that cause limb hypertrophy or loss of function, and painful lesions. Participants with paraspinal PNs will be eligible for this study. Histologic confirmation of tumor is not necessary in the presence of consistent clinical and radiographic findings but should be considered if malignant degeneration of a PN is clinically suspected;
    3.1. For participants enrolled for tumor progression, progression is defined as:
        3.1.1. A measurable increase in PN size (≥20% increase in volume) documented by comparison of two MRI scans in the time period of 12 months or less prior to first dose of study treatment (mirdametinib).
    3.2. For participants enrolled for a "major deformity" or "significantly disfiguring" tumor, eligible tumors will be limited to tumors of the head and neck or those on other areas of the body that are unable to be concealed by standard garments.
4. Participant has a PN that is deemed inoperable, defined as a PN that cannot be completely surgically removed without risk for substantial morbidity due to: encasement of or close proximity to vital structures, invasiveness, or high vascularity of the PN, or the participant refuses surgery. Participants who previously underwent surgery for a PN will be eligible to enter the study after the surgery, provided the PN was incompletely resected and is evaluable by volumetric analysis.
5. Participants must have a target PN, defined as the clinically most relevant PN, amenable to volumetric MRI analysis. For the purpose of this study, the target PN must be seen on at least 3 consecutive MRI slices and the field of view must contain the entire tumor of interest. As determined by central radiologic review, a target PN must be analyzable by volumetrics, at least 5 mL in volume, and will be classified as "typical PN", "nodular PN", or "solitary nodular PN" prior to first dose of study treatment.
6. Participants ≥18 years of age must have a PN amenable to a percutaneous biopsy and must be willing to undergo pre-, and on treatment tumor biopsies providing fresh tumor tissue; there should be no contraindication for serial biopsy; Patients 2 to 17 years of age should not undergo biopsy unless there is a clinical indication to obtain fresh tumor tissue.
7. Participants ≥16 years of age must have a Karnofsky performance level of ≥60%, and participants <16 years must have a Lansky performance of ≥60%.
8. Participant has adequate organ and bone marrow function as defined by the following screening laboratory values:
    8.1. Absolute neutrophil count ≥1500 cells/μL;
    8.2. Platelets ≥100×10$^3$/μL;
    8.3. Hemoglobin ≥9.5 g/dL;
    8.4. Serum albumin ≥2.8 g/dL;
    8.5. Calculated creatinine clearance at Screening ≥60 mL/min (by Cockcroft-Gault formula) OR a normal serum creatinine based on age described in the table below.

| Age (years) | Maximum Serum Creatinine (mg/dL) |
|---|---|
| ≤5 | 0.8 |
| >5 and ≤10 | 1.0 |
| >10 and ≤15 | 1.2 |
| >15 | 1.5 |

9. Participant has the ability to swallow capsules whole.
10. Participant is willing and able to comply with all aspects of the protocol.
11. Participant must weigh at least 10 kg, inclusive, at the time of signing the informed consent/assent.
12. Participant must have a body surface area (BSA) of at least 0.4 m$^2$ (inclusive) calculated using the Du Bois formula (BSA=0.007184×W$^{0.425}$×H$^{0.725}$).
13. Male or Female Contraceptive use by men or women should be consistent with local regulations regarding the methods of contraception for those participating in clinical studies.

a. Male participants:

Male participants are eligible to participate if they agree to the following during the treatment period and for at least 90 days after the last dose of study treatment:

Refrain from donating sperm

PLUS either:

Be abstinent from heterosexual intercourse as their preferred and usual lifestyle (abstinent on a long term and persistent basis) and agree to remain abstinent OR Must agree to use a male condom when having sexual intercourse with a woman of child bearing potential (WOCBP).

b. Female participants:

Female participants are eligible to participate if they are not pregnant or breastfeeding, and at least one of the following conditions applies:

Is not a woman of childbearing potential.

OR

Is a WOCBP and using a contraceptive method that is highly effective (with a failure rate of <1% per year), preferably with low user dependency, during the treatment period and for at least 30 days after the last dose of study treatment and agrees not to donate eggs (ova, oocytes) for the purpose of reproduction during the study and for a period of 90 days.

A WOCBP must have a negative serum pregnancy test result at Screening and a negative urine pregnancy test result at the Baseline visit prior to the first dose of study treatment.

Exclusion Criteria

Participants are excluded from the study if any of the following criteria apply:

1. Participant has a Screening alanine transaminase (ALT) value of >2.0× upper limit of normal (ULN);
2. Participant has a Screening total bilirubin value of >1.5× ULN (isolated bilirubin >1.5× ULN is acceptable if bilirubin is fractionated and direct bilirubin <35%);
3. Participant has a history of malignancy associated hypercalcemia;
4. Participant has an active parathyroid disorder, hyperphosphatemia at Screening (serum phosphorus >1× ULN), and/or serum calcium (mg/dL) x serum phosphorus (mg/dL) product >70 at Screening.
5. Any clinically significant active or known history of liver disease, or known hepatic or biliary abnormalities (with the exception of Gilbert's syndrome or asymptomatic gallstones);
5.1 Hepatitis serology and viral load will be tested at Screening. Patients who are hepatitis B surface antigen (HBsAg) positive or hepatitis C virus (HCV) antibody positive at Screening must not be enrolled until further definite testing with hepatitis B virus (HBV) deoxyribonucleic acid (DNA) titers is <500 IU/mL or HCV ribonucleic acid (RNA) polymerase chain reaction test is negative;
6. Lymphoma, leukemia, or any malignancy (including malignant glioma or malignant peripheral nerve sheath tumor (MPNST)) within the past 5 years except for basal cell or squamous epithelial carcinomas of the skin that have been resected with no evidence of metastatic disease for 3 years;
7. Breast cancer within the past 10 years;
8. Participants with evidence of an active optic glioma or other low-grade glioma, requiring treatment with chemotherapy or radiation therapy. Participants not requiring treatment are eligible. Ophthalmological findings secondary to long-standing optic pathway glioma (such as visual loss, optic nerve pallor or strabismus) or long-standing orbito-temporal PN (such as visual loss, strabismus) will not be considered a significant abnormality for the purposes of the study;
9. Participant has abnormal QT interval corrected by Fridericia's formula (>450 msec for male participants, >470 msec for female participants, or >480 msec for participants with bundle branch block) after electrolytes have been corrected (triplicate ECG readings taken 2 to 3 minutes apart and averaged) at Screening;
10. Participant has experienced any of the following within 6 months (24 weeks) of signing informed consent/assent: clinically significant cardiac disease, myocardial infarction, severe/unstable angina, coronary/peripheral artery bypass graft, cerebrovascular accident, transient ischemic attack, or symptomatic pulmonary embolism;
11. Participant has ever had a recorded left ventricular ejection fraction (LVEF)<55% as assessed by echocardiogram, OR has a history of congestive heart failure;
12. Participant has a history of, or evidence of, retinal pathology on ophthalmologic examination that is considered a risk factor for central serous retinopathy, retinal vein occlusion (RVO), or neovascular macular degeneration. Participants will be excluded from study participation if they currently are known to have any of the following risk factors for RVO:
    12.1 Intraocular pressure ≥21 mmHg;
    12.2 Serum cholesterol >300 mg/dL;
    12.3 Serum triglycerides >300 mg/dL;
    12.4 Hyperglycemia (fasting blood glucose >125 mg/dL or random blood glucose >200 mg/dL);
    12.5 Age specific hypertension
        i. Participants ≥13 years of age with a blood pressure ≥140/90 mm Hg
        ii. Participants ≤12 years of age with a blood pressure ≥95th percentile for age +12 mmHg;
13. Participant has a history of glaucoma;
14. Participant has a history of a positive human immunodeficiency virus (HIV) antibody test;
15. Participant has a known malabsorption syndrome or preexisting gastrointestinal conditions that may impair absorption of mirdametinib (e.g., gastric bypass, lap band, or other gastric procedures). Delivery of mirdametinib via nasogastric tube or gastrostomy tube is not allowed.
16. Participant has received NF1 PN-targeted therapy (e.g., MEK inhibitors, farnesyltransferase inhibitors, kinase inhibitors, etc.) within 28 days of first dose of study treatment (or 5.5 half-lives, whichever is longer). If participant enrolls with progression and no associated morbidities, NF1-targeted therapy must not be administered after the observed progression (Inclusion Criterion 3.1.1). All toxicities from prior therapy must resolve to ≤Grade 1 or Baseline;
17. Participant previously received or is currently receiving therapy with mirdametinib;
18. Participant is receiving systemic or ocular glucocorticoid therapy (with the exception of participants with endocrine deficiencies who are allowed to receive physiologic or stress doses of steroids, if necessary) within 14 days prior to first dose of study treatment;
19. Participant has received radiation therapy within the 6 months prior to signing of informed consent/assent. Participants who have received radiation to the orbit at any time are excluded;
20. Current enrollment or past participation in any other clinical study (excluding observational studies) within 28 days of signing of informed consent/assent;
21. Participant is unable to tolerate MRI or for whom MRI is contraindicated;
22. Tumor is not able to be reliably evaluated by MRI volumetric analysis;

23. Sensitivity to the study treatment, or components thereof, or drug or other allergy that, in the opinion of the investigator or medical monitor, contraindicates participation in the study;
24. Participant with active bacterial, fungal, or viral infection including but not limited to the use of antibiotics, antifungals, or antiviral agents at the time of screening;
25. Underlying medical conditions, laboratory abnormality, or alcohol or drug abuse or dependence that, in the investigator's opinion, will be unfavorable for the administration of study treatment or affect the explanation of drug toxicity or adverse events; or insufficient compliance during the study according to investigator's judgement; or
26. Participant has experienced other severe acute or chronic medical or psychiatric conditions, including recent (within 1 year of signing informed consent/assent) or active suicidal ideation or behavior, or a laboratory abnormality that may increase the risk associated with study participation or study treatment administration or may interfere with the interpretation of study results and, in the judgment of the Investigator, would make the participant inappropriate for entry into this study.

Supportive Care
Dermatologic Adverse Events:

The use of medications for the supportive care of rash is permitted. Early initiation of treatment for rashes is strongly recommended to minimize the duration and severity of the adverse event.

Acneiform rash: Pustular rash may be treated with topical clindamycin gel or lotion applied BID. In severe cases, semisynthetic oral tetracyclines such as doxycycline or minocycline may also be useful for older children, adolescents, and adults, but should be avoided in children younger than 8 years old because of risk to tooth development.

Eczematous rash/xerosis: Eczematous/dry skin rash and other macular (non-acneiform) rash should be treated with a moisturizer such as Cerave or Eucerin or another equivalent product. A low potency topical steroid such as betamethasone valerate lotion (0.05%), desonide cream (0.05%), fluocinolone acetonide solution (0.01%), dexamethasone sodium phosphate cream (0.1%), hydrocortisone acetate cream (1%), methylprednisolone acetate cream (0.25%) or equivalent may also be used if symptomatic.

Ketoconazole Shampoo should be Used for any Rash Involving the Scalp.

Paronychia: Paronychia if acute and non-surgical (i.e., no fluctuance suggesting an abscess) can resolve with warm soaks only applied 3 to 4 times daily. If there is extensive redness suggesting cellulitis, OR if there is non-surgical paronychia but the participant is a diabetic or is immunocompromised, then an oral antibiotic that covers *Staphylococcus aureus* should be started. The choice of antibiotics includes a *Staphylococcus aureus* covering penicillin/clindamycin/first generation cephalosporin/Augmentin (amoxicillin and clavulanate).

If an abscess develops, surgical treatment with incision and drainage with or without debridement should be done. Any infectious organisms identified should be treated accordingly. If the participant has diabetes or is immune compromised, oral antibiotics ensuring coverage for Staphylococcal *aureus* (see above) should be started prior to a culture and sensitivity report. Once culture report is obtained, the antibiotic therapy should be adjusted as appropriate.

Prohibited or Restricted Concomitant Medications/Treatments

Prior use of mirdametinib is prohibited.

Alternative therapy for the treatment of PNs (e.g. MEK inhibitors, farnesyltransferase inhibitors, kinase inhibitors, etc.) within 28 days (or 5.5 half-lives, whichever is longer) of first dose of study treatment and throughout the treatment period is prohibited. If participant enrolls with progression and no associated morbidities, NF1-targeted therapy must not be administered after the observed progression (Inclusion Criterion 3.1.1)

Medical treatment (e.g. chemotherapy, biologic therapy, radiation therapy) directed towards any NF1-related tumor such as optic pathway glioma is prohibited throughout the treatment period.

The use of chronic systemic or ocular glucocorticoid therapy is prohibited within the 14 days prior to first dose of study treatment and throughout the treatment period (with the exception of participants with endocrine deficiencies who are allowed to receive physiologic or stress doses of steroids, if necessary). In addition, corticosteroids are permissible as premedication for blood product transfusions, or as treatment for an acute allergic reaction or bronchospasm.

Pharmacokinetics

General mirdametinib pharmacokinetic parameters are summarized in Table A.

TABLE A

| Pharmacokinetic Parameters and Characteristics of Mirdametinib | | |
|---|---|---|
| Steady-state exposure [geometric mean (geometric % CV)] | Cmax | Adult patients (≥18 years): 188 (52%) ng/mL |
| | | Pediatric patients (2 to <18 years): 191 (62%) ng/ml |
| | AUClast | Adult patients (>18 years): 431 (43%) ng:h/mL |
| | | Pediatric patients (2 to <18 years): 459 (46%) ng h/mL |
| Time to steady-state | | Approximately 6 days |
| Accumulation ratio (AUC) [mean] | | 1.1 to 1.9 over 21 days of BID administration |
| Absorption | | |
| Tmax [median (range)] | | Tablet: 0.83 (0.42-3.02) hours post dose |
| | | Capsule: 1.08 (0.00-4.17) hours post dose |
| Absolute bioavailability | | No data are available in humans |
| Food effect [GMR% (90% CI)] | Cmax | 57% (54%, 61%) |
| | AUCinf | 93% (90%, 96%) |

TABLE A-continued

Pharmacokinetic Parameters and Characteristics of Mirdametinib

| Distribution | |
|---|---|
| Human plasma protein binding | Greater than 99% |
| Apparent volume of distribution [Mean (% CV)] | 255 L (13%) |
| Elimination | |
| Apparent systemic clearance [Mean (% CV)] | 6.34 L/h (13%) |
| Terminal elimination half-life [Mean (% CV)] | 28 h (12%) |
| Metabolism | |
| Primary pathway | Metabolism involves glucuronidation and oxidation via UGT and CES enzymes |
| Excretion | |
| Radioactivity | In urine: 68% |
| | In feces: 27% |
| Unchanged mirdametinib | In urine and feces: 9% |
| | In urine: 0.7% |

Abbreviations:
AUC = area under the plasma concentration-time curve;
AUCinf = AUC from dosing extrapolated to infinity;
AUClast = AUC from time zero to last measurable concentration;
BID = twice daily;
C = cycle;
CI = confidence interval;
CES = carboxyl esterase enzyme;
Cmax = maximum plasma concentration;
CV = coefficient of variability;
D = day;
GMR = geometric lease squares mean ratio The major efficacy outcome measure was confirmed objective response rate (ORR), defined as the percentage of patients with complete response (disappearance of the target PN) or confirmed partial response (≥20% reduction in PN volume confirmed at a subsequent tumor assessment within 2-6 months during the 24-cycle treatment phase). Responses were assessed by blinded independent central review (BICR) using volumetric magnetic resonance imaging (MRI) analysis per Response Evaluation in Neurofibromatosis and Schwannomatosis (REINS) criteria. A secondary efficacy objective was to determine the duration of response for patients who achieved a confirmed objective response.

Efficacy results are provided in Table B. The median time to onset of response was 7.8 months (range: 4.0 months to 19.0 months) for the adult cohort and 7.9 months (range: 4.1 months to 18.8 months) for the pediatric cohort.

TABLE B

Efficacy results

| | Adult (N = 58) | Pediatric (N = 56) |
|---|---|---|
| Confirmed Objective Response Rate per REINS criteria by BICR[i),ii)], n (%) | 24 (41) | 29 (52) |
| 95% CI[iii)] | (29, 55) | (38, 65) |
| p-value[iv)] | <0.001 | <0.001 |

TABLE B-continued

Efficacy results

| | Adult (N = 58) | Pediatric (N = 56) |
|---|---|---|
| Confirmed Complete Response, n (%) | 0 | 0 |
| Confirmed Partial Response, n (%) | 24 (41) | 29 (52) |
| DoR ≥ 12 months[v)] | 18 (75 %) | 22 (76%) |

Abbreviations:
CI = confidence interval;
NR = not reached
[i)]Confirmed objective response was defined as two consecutive assessments of PR or CR assessed by a BICR within 2-6 months during the Treatment Phase
[ii)]Patients who had no post-baseline MRI assessment or no confirmed objective response were treated as non-responders.
[iii)]Obtained using the Clopper-Pearson approach.
[iv)]p-values were calculated using a one-sample two-sided binomial test compared to the minimally clinically relevant response rates of 23% for the adult cohort and 20% for the pediatric cohort.
[v)]Duration of response (data cut-off, September 2023) was assessed using the Kaplan-Meier based approach.

An efficacy analysis that also considered patients who achieved a confirmed objective response after cycle 24 resulted in an ORR of 45% in adults (95% CI: 32, 59) and 54% (95% CI: 40, 67) in pediatric patients.

Example 2: Mirdametinib Treatment for NF1 Patients

Adult and pediatric patients 2 years of age and older with neurofibromatosis type 1 (NF1) who have symptomatic plexiform neurofibromas (PN) are treated as follows. Patients are orally administered mirdametinib trice daily (approximately every 12 hours) for the first 21 days of each 28-day cycle. The maximum dose is 4 mg twice daily. Treatment with mirdametinib is continued until PN progression or unacceptable toxicity.

Mirdametinib is available as two dosage forms: capsules (e.g., 1 or 2 mg capsules) or tablets for oral suspension (e.g., 1 mg tablets for oral suspension). Mirdametinib capsules can be swallowed whole. Mirdametinib tablets for oral suspension can be swallowed whole or can be dispersed in drinking water and administered orally as a liquid.

The dose of mirdametinib is based on body surface area (BSA) as shown in Table 1 below.

TABLE 1

Dose of Mirdametinib

| Body Surface Area*($m^2$) | Recommended Dosage for Capsules or Tablets for Oral Suspension |
|---|---|
| 0.40 to 0.69 | 1 mg twice daily |
| 0.70 to 1.04 | 2 mg twice daily |
| 1.05 to 1.49 | 3 mg twice daily |
| ≥1.50 | 4 mg twice daily |

Dose reductions for mirdametinib for adverse reactions are provided in Table 2 below.

TABLE 2

Dose Reductions for Adverse reactions

| Body Surface Area ($m^2$) | Reduced Dosage | |
|---|---|---|
| | Morning | Evening |
| 0.4 to 0.69 | 1 mg | — |
| 0.7 to 1.04 | 2 mg | 1 mg |
| 1.05 to 1.49 | 2 mg | 2 mg |
| ≥1.5 | 3 mg | 3 mg |

The dose of mirdametinib should be modified from that in Table 1 upon adverse reactions as indicated Table 3 below. The reduced dose in Table 3 refers to the reduced dose in Table 2.

TABLE 3

Dose Modifications for Adverse Reactions

| Severity of Adverse Reaction[1] | Recommended Dose Modification for Mirdametinib |
|---|---|
| Ocular Toxicity | |
| Symptomatic Retinal Pigment Epithelium Detachment | Withhold until resolution. Resume at reduced |
| Retinal Vein Occlusion (RVO) | Permanently discontinue |
| Decreased LVEF | |
| Asymptomatic, absolute decrease in LVEF of 10% or greater from baseline and is less than the lower limit of normal | Withhold until improvement. Resume at reduced dose. |
| For any absolute decrease in LVEF 20% or greater from baseline. | Permanently discontinue |
| Skin Toxicity | |
| Grade 3 or 4 Dermatitis Acneiform or Rash | Withhold until improvement. Resume at reduced. |
| Other Adverse Reactions | |
| Intolerable Grade 2 Grade 3 | Withhold until improvement. Resume at reduced dose. |
| Grade 4 | Withhold until improvement. Resume at reduced dose. Consider discontinuation |

[1]The severity of adverse reactions in Table 3 is per National Cancer Institute Common Terminology Criteria for Adverse Events version 5.0 (NCI CTCAE v. 5.0).

Mirdametinib can be taken with or without food.

If a patient misses a dose of mirdametinib, the patient should resume treatment at the next scheduled dose and not take an additional dose.

If vomiting occurs after mirdametinib administration, do not take an additional dose, but continue with the next scheduled dose.

Mirdametinib Capsules (for example, each capsule contains 1 mg or 2 mg mirdametinib): Patients are to swallow mirdametinib capsules whole. Do not open, break or chew capsules. Do not administer to patients who are unable to swallow a whole capsule.

Mirdametinib tablets for oral suspension (for example, each capsule contains 1 mg mirdametinib): mirdametinib tablets for oral suspension can be swallowed whole or can be dispersed in drinking water and administered orally as liquid.

If dosing as an oral suspension, patients are to fully disperse the prescribed number of tablet(s) in a small amount of drinking water (about 5 to 10 mL) in a dosing cup. Gently swirl the liquid until no lumps remain and administer the dose within 30 minutes of preparation. Alternatively, the liquid can be drawn into an oral syringe and administered. After swallowing the suspension from the dosing cup or oral syringe, rinse the dosing cup (or syringe) with an additional small amount of drinking water (~ 5 to 10 mL) and administer to ensure the full dose is taken. Only use water to prepare the dose.

Assess ejection fraction (including LVEF) by echocardiogram prior to initiating treatment with mirdametinib, every 3 months during the first year, then as clinically indicated thereafter. Withhold, reduce dose, or permanently discontinue mirdametinib based on severity of the adverse reaction.

Conduct comprehensive ophthalmic assessments prior to initiating mirdametinib, at regular intervals during treatment, and for new or worsening visual changes such as blurred vision. Permanently discontinue mirdametinib in patients with retinal vein occlusion (RVO). Withhold mirdametinib in patients with symptomatic retinal pigment epithelium detachment (RPED) until resolution and resume mirdametinib at a reduced dose. For other ocular effects, withhold, reduce dose, or permanently discontinue mirdametinib based on the severity of the adverse reaction.

Initiate supportive care at first signs of skin toxicity. Withhold, reduce dose, or permanently discontinue mirdametinib based on the severity of adverse reaction.

Advise females of reproductive potential to use highly effective contraception during treatment with mirdametinib and for 1 week after the last dose. Advise women not to breastfeed during treatment with mirdametinib and for 1 week after the last dose. Advise males with female partners of reproductive potential to use highly effective contraception during treatment with mirdametinib and for 1 week after the last dose.

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

What is claimed:

1. A method of administering mirdametinib to a human patient in need thereof comprising orally administering to the patient mirdametinib or a pharmaceutically acceptable salt thereof, wherein
   (i) for a patient having a body surface area of 0.4 to 0.69 m$^2$, the patient is initially administered 1 mg mirdametinib or a pharmaceutically acceptable salt thereof twice daily,
   (ii) for a patient having a body surface area of 0.7 to 1.04 m$^2$, the patient is initially administered 2 mg mirdametinib or a pharmaceutically acceptable salt thereof twice daily,
   (iii) for a patient having a body surface area of 1.05 to 1.49 m$^2$, the patient is initially administered 3 mg mirdametinib or a pharmaceutically acceptable salt thereof twice daily, and
   (iv) for a patient having a body surface area of at least 1.5 m$^2$, the patient is initially administered 4 mg mirdametinib or a pharmaceutically acceptable salt thereof twice daily, and wherein the method further comprises:
   (a) upon the patient exhibiting an asymptomatic, absolute decrease in left ventricle ejection fraction (LVEF) of 10% or greater from baseline and is below the lower limit of normal (LLN), withholding the mirdametinib or pharmaceutically acceptable salt thereof until improvement and then restarting administration of the mirdametinib or pharmaceutically acceptable salt thereof at a reduced dose; and
   wherein the reduced dose is:
   (i) for a patient having a body surface area from 0.4 to 0.69 m$^2$, 1 mg once daily,
   (ii) for a patient having a body surface area from 0.7 to 1.04 m$^2$, 2 mg in the morning, and 1 mg in the evening,
   (iii) for a patient having a body surface area from 1.05 to 1.49 m$^2$, 2 mg in the morning and 2 mg in the evening, and
   (iv) for a patient having a body surface area greater than or equal to 1.5 m$^2$, 3 mg in the morning and 3 mg in the evening.

2. The method of claim 1, wherein the patient suffers from a tumor or cancer.

3. The method of claim 2, where the tumor or cancer is selected from the group consisting of plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain.

4. The method of claim 1, wherein (a) upon the patient exhibiting an asymptomatic, absolute decrease in LVEF of 10% or greater and no more than 20% from baseline and is below the LLN, withholding the mirdametinib or pharmaceutically acceptable salt thereof until the absolute decrease in LVEF is resolved and then restarting administration of the mirdametinib or pharmaceutically acceptable salt thereof at the reduced dose.

5. The method of claim 1, wherein the mirdametinib or pharmaceutically acceptable salt thereof is administered with or without food.

6. The method of claim 1, wherein if a patient misses a dose of mirdametinib, the patient skips that dose and resumes administration at the next scheduled dose.

7. The method of claim 1, wherein if vomiting occurs after administering a dose of mirdametinib, the patient does not administer an additional dose of mirdametinib, but continues with administration at the next scheduled dose.

8. The method of claim 1, wherein the mirdametinib or pharmaceutically acceptable salt thereof is administered for the first 21 days of each 28-day cycle.

9. The method of claim 1, wherein the mirdametinib or pharmaceutically acceptable salt thereof is administered until plexiform neurofibromas progression or unacceptable toxicity.

10. The method of claim 1, wherein the LVEF of the patient is assessed by echocardiogram prior to initiating treatment with mirdametinib and every 3 months during the first year of treatment with mirdametinib.

11. The method of claim 1, wherein the patient has symptomatic plexiform neurofibromas.

12. The method of claim 1, wherein the patient has progressive plexiform neurofibromas.

13. The method of claim 1, wherein the patient has head and neck lesions that are compromising the airway or great vessels, brachial or lumbar plexus lesions that are causing nerve compression and loss of function, lesions causing major deformity or are significantly disfiguring, lesions of the extremity that cause limb hypertrophy or loss of function or painful lesions.

14. The method of claim 1, wherein the patient has paraspinal lesions.

15. The method of claim 1, wherein the patient exhibits, at steady state exposure from administration of mirdametinib or a pharmaceutically acceptable salt thereof, a $C_{max}$ of mirdametinib of from about 100 to about 500 ng/mL, prior to withholding the mirdametinib or pharmaceutically acceptable salt thereof.

16. The method of claim 1, wherein the patient exhibits, at steady state exposure from administration of mirdametinib or a pharmaceutically acceptable salt thereof, a $C_{max}$ of mirdametinib of from about 130 to about 245 ng/ml, prior to withholding the mirdametinib or pharmaceutically acceptable salt thereof.

17. The method of claim 1, wherein the patient exhibits, at steady state exposure from administration of mirdametinib or a pharmaceutically acceptable salt thereof, a $AUC_{last}$ of mirdametinib of from about 200 to about 720 ng h/mL, prior to withholding the mirdametinib or pharmaceutically acceptable salt thereof.

18. The method of claim 1, wherein the patient exhibits, at steady state exposure from administration of mirdametinib or a pharmaceutically acceptable salt thereof, a $AUC_{last}$ of mirdametinib of from about 250 to about 610 ng h/mL, prior to withholding the mirdametinib or pharmaceutically acceptable salt thereof.

\* \* \* \* \*